(12) United States Patent
Huber et al.

(10) Patent No.: US 7,169,298 B2
(45) Date of Patent: Jan. 30, 2007

(54) METHOD AND APPARATUS FOR SEPARATING POLYNUCLEOTIDES USING MONOLITHIC CAPILLARY COLUMNS

(75) Inventors: Christian Huber, Rum (AT); Herbert Oberarcher, Natters (AT); Andreas Premstaller, Meran (IT)

(73) Assignee: Transgenomic, Inc., Omaha, NE (US)

( * ) Notice: Subject to any disclaimer, the term of this patent is extended or adjusted under 35 U.S.C. 154(b) by 100 days.

(21) Appl. No.: 09/770,410

(22) Filed: Jan. 25, 2001

(65) Prior Publication Data

US 2002/0088753 A1    Jul. 11, 2002

Related U.S. Application Data

(60) Provisional application No. 60/178,553, filed on Jan. 26, 2000.

(51) Int. Cl.
*B01D 15/08* (2006.01)
(52) U.S. Cl. .............................. 210/198.2; 210/502.1; 210/635; 210/656; 502/402
(58) Field of Classification Search ................ 210/635, 210/656, 659, 198.2, 502.1; 435/6; 502/401, 502/402, 404; 536/25.4
See application file for complete search history.

(56) References Cited

U.S. PATENT DOCUMENTS

| | | | |
|---|---|---|---|
| 4,563,510 A | 1/1986 | Ugelstad | |
| 5,098,539 A | 3/1992 | Shieh | |
| 5,310,463 A | 5/1994 | Dadoo et al. ............ | 204/180.1 |
| 5,316,680 A | 5/1994 | Frechet et al. | |

(Continued)

FOREIGN PATENT DOCUMENTS

EP    0 507 591 A2    10/1992

(Continued)

OTHER PUBLICATIONS

All-Chrom Newsletter Metal Components, A Potential Source of Interference in HPLC Analysis, Alltech-Applied Science, vol. 25, 1:1-6 (1986).

(Continued)

*Primary Examiner*—Ernest G. Therkorn
(74) *Attorney, Agent, or Firm*—Licata & Tyrrell P.C.

(57) ABSTRACT

Methods and devices based on capillary monolithic columns, preferably consisting of an underivatized poly(styrene-divinylbenzene) monolith, for separating a mixture of polynucleotides by ion pair-reverse phase-high performance chromatography (IP-RP-HPLC). In various aspects of the method and device the monolith is characterized by one or more of the following: the monolith is contained within a capillary tube; the monolith is immobilized by covalent attachment at the inner wall of the tube; the tube is devoid of retaining frits; the monolith is characterized by having above 10,000 theoretical plates per meter and preferably above 200,000 theoretical plates per meter; the method uses a mobile phase which is devoid of EDTA; the monolith has a surface morphology that is rugulose or brush-like; the chromatographic surfaces of the monolith are non-porous; the monolith has channels sufficiently large for convective flow of the mobile phase; the monolith is formed from a polymerization mixture including underivatized styrene, a crosslinking agent, and a porogen, wherein the porogen includes tetrahydrofuran. The monolith can be incorporated into a miniaturized chromatography system which can be coupled to a mass spectrometer for on-line separation and mass determination of single- or double-stranded polynucleotides.

38 Claims, 10 Drawing Sheets

U.S. PATENT DOCUMENTS

| | | | |
|---|---|---|---|
| 5,334,310 A | 8/1994 | Frechet et al. | 210/198.2 |
| 5,338,448 A | 8/1994 | Gjerde | |
| 5,342,492 A | 8/1994 | Dadoo et al. | 204/180.1 |
| 5,378,334 A | 1/1995 | Dadoo et al. | 204/180.1 |
| 5,423,513 A | 6/1995 | Chervet et al. | 250/227.2 |
| 5,453,185 A | 9/1995 | Frechet et al. | 210/198.2 |
| 5,522,994 A | 6/1996 | Frechet et al. | |
| 5,583,162 A | 12/1996 | Li et al. | |
| 5,585,236 A | 12/1996 | Bonn et al. | 435/5 |
| 5,645,717 A | 7/1997 | Hjerten et al. | |
| 5,647,979 A | 7/1997 | Liao et al. | |
| 5,728,457 A | 3/1998 | Frechet et al. | |
| 5,772,889 A | 6/1998 | Gjerde et al. | |
| 5,929,214 A * | 7/1999 | Peters | 530/417 |
| 5,935,429 A | 8/1999 | Liao et al. | 210/198.2 |
| 5,972,222 A | 10/1999 | Gjerde et al. | |
| 5,998,604 A | 12/1999 | Fearon et al. | 536/25.4 |
| 6,024,878 A | 2/2000 | Gjerde et al. | 210/635 |
| 6,045,697 A * | 4/2000 | Girot | 210/635 |
| 6,063,589 A | 5/2000 | Kellogg et al. | 435/24 |
| 6,066,258 A | 5/2000 | Gjerde et al. | |
| 6,174,441 B1 | 1/2001 | Gjerde et al. | |
| 6,238,565 B1 | 5/2001 | Hatch | 210/635 |
| 6,355,791 B1 | 3/2002 | Gjerde et al. | 536/25.4 |
| 6,372,130 B1 * | 4/2002 | Gjerde | 210/198.2 |
| 2002/0017487 A1 | 2/2002 | Huang | 210/635 |

FOREIGN PATENT DOCUMENTS

| | | | | |
|---|---|---|---|---|
| EP | 0597552 A1 | 5/1994 | | 210/635 |
| EP | 0 813 062 A2 | 1/1997 | | |
| WO | WO 90/07965 | 7/1990 | | 210/635 |
| WO | WO 94/11305 | 5/1994 | | |
| WO | WO 95/34359 | 12/1995 | | |
| WO | WO 97/19347 | 5/1997 | | |
| WO | WO 98/40395 | 9/1998 | | 210/635 |
| WO | WO 00/15778 | 3/2000 | | 210/635 |
| WO | WO 01/55713 A2 | 8/2001 | | 210/635 |
| WO | WO 01/83072 | 11/2001 | | |

OTHER PUBLICATIONS

Apffel et al, Analysis of Oligonucleotides by HPLC-Electrospray Ionization Mass Spectrometry, Anal. Chem. 1997, 69, 1320-1325.
Cabrera et al., SilicaROD—A New Challenge in Fast High-Performance Liquid Chromatography Separations, Trends in Analytical Chemistry, vol. 17, No. 1, pp. 50-53 (1998).
Colon et al., Capillary Electrochromatography, Anal. Chem. News & Features, 461A-467A (1997).
Engelhardt et al., Polymer Encapsulated Stationary Phases: Advantages, Properties and Selectivities, Chromatographia, No. 11/12 , 27:535-543 (1989).
Heftman, Chromatography, 5th Edition, Journal of Chromatography Library , Elsevier, 51:A-299-A300 (1992).
Hjerten et al., High-Performance Liquid Chromatography on Continuous Polymer Beds, Journal of Chromatography, 473:273-275 (1989).
Huber et al., Micropellicular Stationary Phases for High-Performance Liquid Chromatography of Double-Stranded DNA, J. of Chromatography A, 806:1-28 (1998).
Huber et al., Evaluation of Volatile Eluents and Electrolytes for High-Performance Liquid Chromatography—. . . , Journal of Chromatography A, 849:161-173 (1999).
Leonard, M., New Packaging Materials for Protein Chromatography, Journal of Chromatography B, 699:3-27 (1997).
Liao et al., Continuous Beds for Microchromatography: Reversed -Phase Chromatography, Analytical Biochemistry, 234:27-30 (1996).
Moore, Roger E., et al. Anal. Chem., 70:4879-4884 (1998).
Tennikova, Tatiana B., et al. J. High Resol. Chromatogr. 23:27-38 (2000).

Wang et al., Reversed-Phase Chromatography of Small Molecules and Peptides Ona Continous Rod of Macrophorous Poly(Styrene-Codivinylbenzene), Journal of Chromatography, 669:230-235 (1994).
Afeyan et al. J. Chromatogr., 519:1-29 (1990).
Dadoo et al. Advances Toward the Routine Use of Capillary Electrochromatography, LC-GC, 15:630-635 (1997).
Ericson et al. Preparation of Continuous Beds for Electrochromatography and Reversed-Phase Liquid Chromatography of Low-Molecular-Mass, Journal of Chromatography A, 767:33-41 (1997).
Fields, Silica Xerogel as a Continuous Column Support for High-Performance Liquid Chromatography Anal. Chem., 68:2709-2712 (1996).
Fujimoto et al. Fritless Packed Columns for Capillary Electrochromatography: Separation of Uncharged Compounds on Hydrophobic Hydrogels, Anal. Chem., 68:2753-2757 (1996).
Fujimoto et al. Capillary Electrochromatography of Small Molecules in Polyacryamide Gels with Electroosmotic Flow, Journal of Chromatography A, 716 107-113 (1995).
Griffey et al. Characterization of Oligonucleotide Metabolism in Vivo Via Liquid Chromatography/Electrosspray Tandem Mass Spectrometry with a Quadrupole Ion Trap Mass Spectrometry, Journal of Mass Spectrometry, 32: 305-313 (1997).
Grim, Capillary LC With Automated On-Line Microfraction Collection Onto Maldi/Tof MS Tragets, Int. Biotechnol. Laboratory, Oct. 1997, p. 58.
Gusev et al. Capillary Columns with in Situ Formed Porous Monolithic Packing for Micro High-Performance Liquid Chromatography and Capillary Electrochromatography, Journal of Chromatography A, 855: 273-290 (1999).
He et al. Fabrication of Nanocolumns for Liquid Chromatography, Anal. Chem., 70: 3790-3797 (1998).
Hirata et al. J. Chromatogr., 186:521-528 (1979).
Hjerten et al. Continuous Beds: High-Resolving, Cost-Effective Chromatographic Matrices, Nature, 356:810-811 (1992).
http://www.lcpackings.nl (Apr. 14, 2000) pp. 1-48.
Huang et al. Capillary Zone Electroporesis With Fluid-Impervious Polymer Tubing Inside a Fused-Silica Capillary, Journal of Chromatography A, 788: 155-164 (1997).
Huang et al. Surface-Alkylated Polystyrene Monolithic Columns for Peptide Analysis in Capillary Liquid Chromatography-Electrospray Ionization Mass Spectrometry, Anal. Chem., 74: 2336-2344 (2002).
Huber et al. High-Resolution Liquid Chromatography of Oligonucleotides on Nonporous Alkylated Styrene-Divinylbenzene Copolymers, Analytical Biochemistry, 212:351-358 (1993).
Huber et al. On-Line Cation Exchange for Suppression of Adduct Formation in Negative-Ion Electrospray Mass Spectrometry of Nucleic Acids, Anal. Chem., 70: 5288-5295 (1998).
Huber et al. Analysis of Nucleic Acids by Capillary Ion-Pair Reversed-Phase HPLC Coupled to Negative-Ion Electrospray Ionization Mass Spectrometry, Anal. Chem., 71:3730-3739 (1999).
Huber et al. Rapid and Accurate Sizing of DNA Fragments by Ion-Pair Chromatography on Alkylated Nonporous Poly(Styrene-Divinylbenzene) Particles, Analytical Chemistry, 67:578-585 (1995).
Huber et al. Sheath Liquid Effects Capillary High-Performance Liquid Chromatography-Electrospray Mass Spectrometry of Oligonucleotides, Journal of Chromatography A, 870:413-424 (2000).
Huber et al. A Comparison of Micropellicular Anion-Exchange and Reversed-Phase Stationary Phases for HPLC Analysis of Oligonucleotides, LC-GC, 14:114-127 (1996).
Huber et al. Mutation Detection by Capillary Denaturing High-Performance Liquid Chromatography Using Monolithic Columns, J. Biochem. Biophys Methods, 47:5-19 (2001).
Ishizuka et al. Chromatography Properties of Miniaturized Silica Rod Columns, J. High Resol. Chromatogr., 21:477-479 (1998).
Jorgenson et al. High-Resolution Sepration Based on Electroph0resis and Electroosmosis, J. of Chromatography, 218:209-216 (1981).
Karlsson et al. Anal. Chem., 60:1662-1665 (1988).

Kennedy et al. Anal. Chem., 61:1128-1135 (1989).

Martin et al. Biochem J., 35:1358 (1941).

McGuffin et al. Anal. Chem., 55:580-583 (1983).

McLuckey et al. Tandem Mass Spectrometry of Small, Multiply Charged Oligodeoxynucleotides, 3:60-70 (1992).

Minakuchi et al. Octadecylsilylated Porous Silica Rods as Separation Media for Reversed-Phase Liquid Chromatography, Anal. Chem. 68:3498-3501 (1996).

Muddiman et al. Characterization of PCR Products from *Bacilli* Using Electrospray Ionization FTICR Mass Spectrometry, Anal. Chem., 68:3705-3712 (1996).

Muddiman et al. Precise Mass Measurement of a Double-Stranded 500 Base-Pair (309 kDa) Polymerase Chain Reaction Product by Negative Ion Electrospray Ionization Fourier Transform Ion Cyclotron . . . , Rapid Commun. Mass Spectrom., 13:1201-1204 (1999).

Nordhoff et al. Mass Spectrometry of Nucleic Acids, Mass Spectrometry Reviews, 15:67-138 (1996).

Novotny, J. Chromatogr. B, 689: 55-70 (1997).

Novotony, Anal. Chem., 60:500A-510A (1988).

Oberacher et al. Preparation and Evaluation of Packed Capillary Columns for the Separation of Nucleic Acids by Ion-Pair Reversed-Phase High-Performance Liquid Chromatography, J. of Chrom. A, 893:23-35 (2000).

Palm et al. Macroporous Polyacrylamide/Poly (Ethylene Glycol) Matrixes as Stationary Phases in Capillary Electrochromatography, Anal. Chem., 69:4499-4507 (1997).

Peters et al. Molded Rigid Polymer Monoliths as Separation Media for Capillary Electrochromatography, Anal. Chem., 69:3645-3649 (1997).

Peters et al. Molded Rigid Polymer Monoliths as Separation Media for Capillary Electrochromatography. 2. Effect of Chromatographic Conditions on the Separation, Anal. Chem., 70:2296-2302 (1998).

Petro et al. Molded Monolithic Rod of Macroprous Poly (Styrene-Co-Divinylbenzene) as a Separation Medium for HPLC of Synthetic Polymers . . . , Analytical Chemistry, 68:315-321 (1996).

Petro et al. J. Chromatogr. A, 752:59-66 (1996).

Poole et al. Chromatography Today, Elsevier, Amsterdam (1995).

Potier et al. Nucleic Acids Res., 22:3895-3903 (1994).

Premstaller et al. High-Performance Liquid Chromatography-Electrospray Ionization Mass Spectrometry of Single- and Double-Stranded Nucleic Acids Using Monolithic Capillary Columns Anal. Chem., 72:4386-4393 (2000).

Pretorius et al. A New Concept for High-Speed Liquid Chromatography, J. of Chromatography, 99:23-30 (1974).

Rathore et al. J. Chromatogr. A, 743: 231-246 (1996).

Rodrigues et al. J. Chromatogr., 653:189 (1993).

Scott et al. J. Chromatogr. Sci., 20:62-66 (1982).

Seidl et al. Markroporose Styrol-Divinylbenzol-Copolymere Und Ihre Venwendung in der Chromatographie und zue Darstellung von Ionenaustauschern, Adv. Polymer Sci., 5:113-213 (1967).

Snyder et al. Practical HPLC Method Development Eds., John Wiley & Sons, New York, pp. 40-47 (1997).

Stults et al. Improved Electrospray Ionization of Synthetic Oligodeoxynucleotides, Rapid Communication in Mass Spectrometry, 5:359-363 (1991).

Suck et al. The Structure of a Trinucleoside Diphosphate:Adenylyl-(3',5')-Adenylyl-(3',5')-Adenosine Hexahydrate, Acta Cryst. B, 32:1727-1737 (1976).

Svec et al. Temperature, A Simple and Efficient Tool for the Control of Pore Size Distribution in Macroporous Polymers, Macromolecules, 25:7580-7582 (1995).

Takeuchi et al. J. Chromatogr., 253:41-47 (1982).

Tomer et al. Capillary Liquid Chromatography/Mass Spectrometry, Mass Spectrometry Reviews, 13:431-457 (1994).

Viklund et al. Chem. Mater., 9:463-471 (1997).

Viklund et al. Monolithic, "Molded", Porous Materials with High Flow Characteristics for Separations, Catalysis, or Solid-Phase Chemistry: Control of Porous Properties During Polymerization, Chem. Mater., 8:744-750 (1996).

Wang et al. Anal. Chem., 64:1232-1238 (1992).

Xiao et al. Multiplex Capillary Denaturing High-Performance Liquid Chromatography With Laser-Induced Fluroresence Detection, BioTechniques, 30:1332-1338 (2001).

Polymicro Technologies, LLC. Flexible Fused Silica Capillary Tubing Product Literature. Printed from Corporate website on Sep. 20, 2005.

* cited by examiner

SEQUENCE LISTING

```
<160> NUMBER OF SEQ ID NOS: 1

<210> SEQ ID NO 1
<211> LENGTH: 80
<212> TYPE: DNA
<213> ORGANISM: Artificial Sequence
<220> FEATURE:
<223> OTHER INFORMATION: 80-mer

<400> SEQUENCE: 1
ccccagtgct gcaatgatac cgcgagaccc acgctcaccg gctccagatt tatcagcaat      60
aaaccagcca gccggaaggg                                                  80
```

METHOD AND APPARATUS FOR SEPARATING POLYNUCLEOTIDES USING MONOLITHIC CAPILLARY COLUMNS

CROSS REFERENCE TO RELATED CO-PENDING APPLICATIONS

This application is a regular U.S. patent application under 35 U.S.C. §111(a) and 37 C.F.R. 1.53(b) and claims priority from the following co-pending, commonly assigned provisional application filed under 35 U.S.C. §111(b): Ser. No. 60/178,553 filed Jan. 26, 2000.

FIELD OF THE INVENTION

The present invention relates to methods and devices for analyzing polynucleotides. In particular, the invention relates to the use of monolithic capillary columns for use in high-performance liquid chromatography of single and double-stranded polynucleotides.

BACKGROUND OF THE INVENTION

Genetics and proteomics depend on the ability to analyze complex mixtures of biological origin with high sensitivity and maximum selectivity. Especially the rapid development of miniaturized techniques in analytical chemistry (He et al. *Anal. Chem.* 70:3790–3797 (1998)) has had a profound impact on the modern practice of analyzing biological samples of high complexity (Novotny *J. Chromatogr. B* 689: 55–70 (1997)). Several techniques based on the principle of differential migration (Rathore et al. *J. Chromatogr. A* 743: 231–246 (1996)) were developed after the introduction of fused silica capillaries to analytical chemistry (Dandeneau et al. *HRC & CC:* 2:351 (1979)), in particular capillary liquid chromatography (CLC) (Hirata et al. *J. Chromatogr.* 186: 521–528 (1979)), capillary electrophoresis (CE) (Jorgenson et al. *J. Chromatogr.* 218:209–216 (1981)), and capillary electrochromatography (CEC) (Jorgenson et al. *J. Chromatogr.* 218:209–216 (1981)).

Columns packed with microparticulate sorbents have been successfully applied as separation media in high-performance liquid chromatography (HPLC). Despite many advantages, HPLC columns packed with microparticulate, porous stationary phases have some limitations, such as the relatively large void volume between the packed particles and the slow diffusional mass transfer of solutes into and out of the stagnant mobile phase present in the pores of the separation medium (Martin et a. *Biochem J.* 35:1358 (1941); Unger et al in *Packings and Staionary Phases in Chromatographic Techniques,* Unger Ed: Marcel Dekker: New York, p. 75 (1990)).

One approach to alleviate the problem of restricted mass transfer and intraparticular void volume is the concept of monolithic chromatographic beds, where the separation medium consists of a continuous rod of a rigid, polymer which has no interstitial volume but only internal porosity consisting of micropores and macropores. Monolithic separation columns are becoming more widely used in HPLC of biomolecules.

WO 97/19347 relates to a method and device for separating one or several organic substances in a sample. The chromatographic device comprises a monolith prepared in an emulsion system containing at least 75% by weight of water phase. Separations of polynucleotides were not disclosed.

U.S. Pat. No. 5,334,310 relates to a monolith containing small pores having diameters less than about 200 nm and large pores with diameters greater that about 600 nm. The columns were equipped with end fittings. No separations of polynucleotides were demonstrated.

WO 00/15778 relates to polymeric monolithic beds for resolving mixtures containing polynucleotides. However, single-stranded molecules were poorly resolved using the column. The columns had inner diameters (ID) of greater than 4 mm and were equipped retaining frits. The mobile phase buffers included EDTA. Useful separations of DNA fragments by IP-RP-HPLC using underivatized polystyrene/divinylbenzene monolithic columns could not be achieved and such columns were not recommended.

There is a need for improved monolithic columns and methods for the separation of polynucleotides.

SUMMARY OF THE INVENTION

In one aspect, the present invention provides a method for separating a mixture of polynucleotides. The method includes applying the mixture of polynucleotides to a polymeric monolith having non-polar chromatographic surfaces and eluting the mixture of polynucleotides with a mobile phase including a counterion agent and an organic solvent, wherein the monolith is an underivatized poly(styrene-divinylbenzene) matrix. In the method, the monolith preferably is contained within a fused silica tube having an inner diameter in the range of 1 to 1000 micrometer and the monolith is immobilized by covalent attachment at the inner wall of the tube. The tube is preferably devoid of retaining frits. In preferred embodiments of this aspect of the invention, the monolith is characterized by having 100,000 to 200,000 theoretical plates per meter. The theoretical plates per meter can determined from the retention time of single stranded $p(dT)_{18}$ standard using the following equation:

$$(N/L) = (5.54/L)\left(\frac{t_R}{w_{0.5}}\right)^2$$

wherein N is the number of theoretical plates, $t_R$ is the retention time of said standard determined during an isocratic elution, $w_{0.5}$ is the peak width at half height, and L is the length of the monolith in meters. In one embodiment, during the isocratic elution, the back pressure was about 180 to 200 bar, at a flow rate in the range of 2 to 3 µL/min and at an elution temperature of 50° C. for a monolith having an ID of 200 micrometer and a length of 60 mm. The method can be performed using a mobile phase which is devoid of EDTA. The preferred monolith has a surface morphology, as determined by scanning electron microscopy, that resembles the surface morphology of octadecyl modified poly(styrene-divinylbenzene) particles, wherein the surface morphology of the monolith is rugulose. Additionally, the preferred monolith has a surface morphology, as determined by scanning electron microscopy, that resembles the surface morphology of octadecyl modified poly(styrene-divinylbenzene) particles, wherein the surface morphology of the monolith is brush-like. The monolith can be formed from a polymerization mixture including underivatized styrene, a crosslinking agent, and a porogen, wherein the porogen includes tetrahydrofuran. A preferred porogen includes a mixture of tetrahydrofuran and decanol. In the method, the polynucleotides can include double-stranded fragments having lengths in the range of 3 to 600 base pairs. The method can further include analyzing eluted polynucleotides by mass spectral analysis. In the method, the monolith preferably has a back pressure in the range of about 20 to about 300 bar, and typically in the range of about 70 to about 200 bar. The method can be performed at a monolith temperature in the range of about 20° C. to about 90° C.

In another aspect, the invention concerns a method for separating a mixture of polynucleotides. The method includes applying the mixture of polynucleotides to a polymeric monolith having non-polar chromatographic surfaces and eluting the mixture of polynucleotides with a mobile phase comprising a counterion agent and an organic solvent. In a preferred embodiment, the monolith comprises an underivatized poly(styrene-divinylbenzene) matrix. In this aspect of the invention, the monolith is preferably contained within a fused silica tube, and the monolith is immobilized by covalent attachment at the inner wall of the tube. The tube can have an inner diameter in the range of 10 micrometer to 1000 micrometer, and preferably in the range of 1 micrometer to 1000 micrometer. The tube is preferably devoid of retaining frits. In certain embodiments, the monolith is characterized by having 10,000 to 200,000 theoretical plates per meter and preferably characterized by having 100,000 to 200,000 theoretical plates per meter. During the elution, the mobile phase preferably is devoid of EDTA. The preferred monolith has a surface morphology, as determined by scanning electron microscopy, that resembles the surface morphology of octadecyl modified poly(styrene-divinylbenzene) particles, wherein the surface morphology of the monolith is rugulose. The monolith can be formed from a polymerization mixture including underivatized styrene, a crosslinking agent, and a porogen, wherein the porogen comprises tetrahydrofuran.

In another aspect, the invention provides a method for separating a mixture of polynucleotides. The method includes applying the mixture of polynucleotides to a polymeric monolith having non-polar chromatographic surfaces and eluting the mixture of polynucleotides with a mobile phase comprising a counterion agent and an organic solvent, wherein the monolith comprises an underivatized poly(styrene-divinylbenzene) matrix, wherein the monolith is contained within a fused silica tube, and wherein the tube is devoid of retaining frits, wherein the tube has an inner diameter in the range of 1 micrometer to 1000 micrometer, and wherein the polynucleotides are double-stranded fragments having lengths in the range of 3 to 600 base pairs. During the elution, the mobile phase preferably is devoid of EDTA. The monolith preferably is immobilized by covalent attachment at the inner wall of the tube. In certain embodiments, the monolith is characterized by having 50,000 to 200,000 theoretical plates per meter. In preferred embodiments, the monolith is characterized by having greater than about 190,000 theoretical plates per meter. The preferred monolith has a surface morphology, as determined by scanning electron microscopy, that resembles the surface morphology of octadecyl modified poly(styrene-divinylbenzene) particles, wherein the surface morphology of the monolith is rugulose.

In a further aspect, the invention provides a method for separating a mixture of polynucleotides. The method includes applying the mixture of polynucleotides to a polymeric monolith having non-polar chromatographic surfaces and eluting said mixture of polynucleotides with a mobile phase comprising a counterion agent and an organic solvent, wherein the monolith is characterized by having 10,000 to 200,000 theoretical plates per meter, wherein the monolith includes an underivatized poly(styrene-divinylbenzene) matrix, wherein the monolith is contained within a fused silica tube having an inner diameter in the range of 1 micrometer to 1000 micrometer, and wherein the monolith is immobilized by covalent attachment at the inner wall of the tube. In a preferred embodiment, the theoretical plates per meter is determined from the retention time of single stranded $p(dT)_{18}$ standard using the following equation:

$$(N/L) = (5.54/L)\left(\frac{t_R}{w_{0.5}}\right)^2$$

wherein N is the number of theoretical plates, $t_R$ is the retention time of said standard determined during an isocratic elution, $w_{0.5}$ is the peak width at half height, and L is the length of the monolith in meters. The tube preferably is devoid of retaining frits. In the method, the mobile phase preferably is devoid of EDTA. In a preferred embodiment, the monolith has a surface morphology, as determined by scanning electron microscopy, that resembles the surface morphology of octadecyl modified poly(styrene-divinylbenzene) particles, wherein the surface morphology of said monolith is rugulose. Also in a preferred embodiment, the monolith has a surface morphology, as determined by scanning electron microscopy, that resembles the surface morphology of octadecyl modified poly(styrene-divinylbenzene) particles, wherein the surface morphology of said monolith is brush-like.

In a yet further aspect, the invention concerns a method for separating a mixture of polynucleotides. The method includes applying the mixture of polynucleotides to a polymeric monolith having non-polar chromatographic surfaces and eluting the mixture of polynucleotides with a mobile phase comprising a counterion agent and an organic solvent, and wherein the mobile phase is devoid of EDTA. In this aspect, the monolith preferably is contained within a fused silica tube having an inner diameter in the range of 10 micrometer to 1000 micrometer. The monolith preferably is immobilized by covalent attachment at the inner wall of the tube. The tube preferably is devoid of retaining frits. In certain embodiments of this aspect of the invention, the monolith is characterized by having 10,000 to 200,000 theoretical plates per meter. The preferred monolith has a surface morphology, as determined by scanning electron microscopy, that resembles the surface morphology of octadecyl modified poly(styrene-divinylbenzene) particles, wherein the surface morphology of the monolith is rugulose. The preferred monolith comprises an underivatized poly(styrene-divinylbenzene) matrix.

In a still further aspect, the invention provides a method for separating a mixture of polynucleotides. The method includes applying the mixture of polynucleotides to a polymeric monolith having non-polar chromatographic surfaces and eluting the mixture of polynucleotides with a mobile phase comprising a counterion agent and an organic solvent, wherein the monolith has a surface morphology, as determined by scanning electron microscopy, that resembles the surface morphology of octadecyl modified poly(styrene-divinylbenzene) particles, wherein the surface morphology of the monolith is rugulose, and wherein the monolith comprises an underivatized poly(styrene-divinylbenzene) matrix. The mobile phase preferably is devoid of EDTA. In preferred embodiments, the monolith can be characterized by one or more of the following: the monolith is contained within a fused silica tube having an inner diameter in the range of 1 micrometer to 1000 micrometer; the monolith is immobilized by covalent attachment at the inner wall of the tube; and, the tube is devoid of retaining frits. In preferred embodiments, the monolith is characterized by having 100,000 to 200,000 theoretical plates per meter.

In a related aspect, the invention provides a method for separating a mixture of polynucleotides. In this aspect, the method includes applying the mixture of polynucleotides to a polymeric monolith having non-polar chromatographic surfaces and eluting the mixture of polynucleotides with a mobile phase comprising a counterion agent and an organic solvent, wherein the monolith comprises an underivatized poly(styrene-divinylbenzene) matrix, wherein the monolith is contained within a fused silica tube having an inner diameter in the range of 1 micrometer to 1000 micrometer, wherein the monolith is immobilized at the inner wall of the tube, and wherein the tube is devoid of retaining frits. Preferred embodiments of this aspect of the invention can include one or more of the following: the mobile phase is devoid of EDTA; the monolith is characterized by having 100,000 to 200,000 theoretical plates per meter; and, the monolith has a surface morphology, as determined by scanning electron microscopy, that resembles the surface morphology of octadecyl modified poly(styrene-divinylbenzene) particles, wherein the surface morphology of the monolith is rugulose. The monolith can be formed from a polymerization mixture including underivatized styrene, a crosslinking agent, and a porogen, wherein the porogen comprises tetrahydrofuran. The method can further include analyzing eluted polynucleotides by mass spectral analysis.

In an additional aspect, the invention provides a device for separating a mixture of polynucleotides. The device includes a polymeric monolith having non-polar chromatographic surfaces, wherein the monolith is contained within a fused silica tube having an inner diameter in the range of 1 micrometer to 1000 micrometer, wherein the monolith is immobilized by covalent attachment at the inner wall of the tube, and wherein the monolith comprises an underivatized poly(styrene-divinylbenzene) matrix. Preferred embodiments of this aspect of the invention can be further characterized by the following: the tube is devoid of retaining frits; the monolith is characterized by having 100,000 to 200,000 theoretical plates per meter. The theoretical plates per meter preferably is determined from the retention time of single stranded p(dT)$_{18}$ standard using the following equation:

$$(N/L) = (5.54/L)\left(\frac{t_R}{w_{0.5}}\right)^2$$

wherein N is the number of theoretical plates, $t_R$ is the retention time of said standard determined during an isocratic elution, $w_{0.5}$ is the peak width at half height, and L is the length of the monolith in meters. During the isocratic elution the monolith preferably has a back pressure of 180 to 200 bar, and a flow rate in the range of 2 to 3 μL/min at an elution temperature of 50° C. Preferred embodiments of the device can be characterized by one or more of the following: the chromatographic surfaces of the monolith are non-porous; the monolith has channels sufficiently large for convective flow of said mobile phase; and, the monolith can be formed from a polymerization mixture including underivatized styrene, a crosslinking agent, and a porogen, wherein the porogen comprises tetrahydrofuran.

In a further yet aspect, the invention concerns a device for separating a mixture of polynucleotides. The device includes a polymeric monolith having non-polar chromatographic surfaces, wherein the monolith is contained within a fused silica tube, wherein the monolith is immobilized by covalent attachment at the inner wall of the tube, and wherein the monolith comprises an underivatized poly(styrene-divinylbenzene) matrix. Preferred embodiments can include one or more of the following features: the tube has an inner diameter in the range of 1 micrometer to 1000 micrometer; the tube is devoid of retaining frits; the monolith is characterized by having 10,000 to 200,000 theoretical plates per meter; the monolith comprises an underivatized monolithic stationary phase; the monolith has a surface morphology, as determined by scanning electron microscopy, that resembles the surface morphology of octadecyl modified poly(styrene-divinylbenzene) particles, wherein the surface morphology of the monolith is rugulose; the chromatographic surfaces of the monolith are non-porous; and the particles have channels sufficiently large for convective flow of the mobile phase. The monolith can be formed from a polymerization mixture including underivatized styrene, a crosslinking agent, and a porogen, wherein the porogen comprises tetrahydrofuran.

In another aspect, the invention concerns a device for separating a mixture of polynucleotides. The device includes a polymeric monolith having non-polar chromatographic surfaces, wherein the monolith is contained within a fused silica tube, wherein the tube is devoid of retaining frits, and wherein the monolith comprises an underivatized poly(styrene-divinylbenzene) matrix. Preferred embodiments of this aspect of the invention can further include one or more of the following: the monolith is immobilized by covalent attachment at the inner wall of said tube; the monolith is characterized by having 100,000 to 200,000 theoretical plates per meter; the tube has an inner diameter in the range of 1 micrometer to 1000 micrometer; and, the monolith has a surface morphology, as determined by scanning electron microscopy, that resembles the surface morphology of octadecyl modified poly(styrene-divinylbenzene) particles, wherein the surface morphology of the monolith is rugulose. The monolith can be formed from a polymerization mixture including underivatized styrene, a crosslinking agent, and a porogen, wherein the porogen comprises tetrahydrofuran.

In a related aspect, the invention provides a device for separating a mixture of polynucleotides. The device includes a polymeric monolith having non-polar chromatographic surfaces, wherein the monolith is characterized by having 100,000 to 200,000 theoretical plates per meter, wherein the monolith is contained within a fused silica tube having an inner diameter in the range of 1 micrometer to 1000 micrometer, and wherein the tube has been silianized. Preferred embodiments of this aspect of the invention can further include one or more of the following: the monolith is immobilized by covalent attachment at the inner wall of the tube; the tube is devoid of retaining frits; the monolith comprises an underivatized poly(styrene-divinylbenzene) matrix; and, the monolith has a surface morphology, as determined by scanning electron microscopy, that resembles the surface morphology of octadecyl modified poly(styrene-divinylbenzene) particles, wherein the surface morphology of the monolith is rugulose. The monolith can be formed from a polymerization mixture including underivatized styrene, a crosslinking agent, and a porogen, wherein the porogen comprises tetrahydrofuran.

In an important aspect, the invention provides a device for separating a mixture of polynucleotides. The device includes a polymeric monolith having non-polar chromatographic surfaces, wherein the monolith comprises an underivatized poly(styrene-divinylbenzene) matrix, and wherein the monolith is characterized by having 10,000 to 200,000 theoretical plates per meter. Preferred embodiments of this aspect of the invention can further include one or more of the following: the monolith is contained within a tube having an inner diameter in the range of 1 micrometer to 1000 micrometer; the monolith is immobilized at the inner wall of the tube; the tube is devoid of retaining frits; and, the monolith has a surface morphology, as determined by scanning electron microscopy, that resembles the surface morphology of octadecyl modified poly(styrene-divinylbenzene) particles, wherein the surface morphology of the monolith is rugulose.

In another aspect, the invention provides a miniaturized chromatographic system for separating a mixture of polynucleotides. The device includes a polymeric monolith having non-polar chromatographic surfaces, wherein the monolith comprises an underivatized poly(styrene-divinylbenzene) matrix, wherein the monolith is characterized by having at least 100,000 theoretical plates per meter, wherein the monolith is contained within a tube having an inner diameter in the range of 10 micrometer to 1000 micrometer, and wherein the monolith is immobilized at the inner wall of the tube. Preferred embodiments of this aspect of the invention can further include one or more of the following: the tube is devoid of retaining frits; the monolith is contained within a tube having an inner diameter in the range of 1 micrometer to 1000 micrometer; the monolith has a surface morphology, as determined by scanning electron microscopy, that resembles the surface morphology of octadecyl modified poly(styrene-divinylbenzene) particles, wherein the surface morphology of the monolith is rugulose; and wherein the monolith has a surface morphology, as determined by scanning electron microscopy, that resembles the surface morphology of octadecyl modified poly(styrene-divinylbenzene) particles, wherein the surface morphology of the monolith is brush-like. The monolith can be formed from a polymerization mixture including underivatized styrene, a crosslinking agent, and a porogen, wherein the porogen comprises tetrahydrofuran.

In an additional aspect, the invention concerns a miniaturized chromatographic system for separating a mixture of polynucleotides. The system preferably includes a device which includes a polymeric monolith having non-polar chromatographic surfaces, wherein the monolith comprises an underivatized poly(styrene-divinylbenzene) matrix, wherein the monolith is characterized by having at least 100,000 theoretical plates per meter, wherein the monolith is contained within a tube having an inner diameter in the range of 10 micrometer to 1000 micrometer, and wherein the monolith is immobilized at the inner wall of the tube. In the system, the monolith can be operatively coupled to a mass spectrometer.

In a further aspect, the invention concerns a device for separating a mixture of polynucleotides. The device includes a polymeric monolith having non-polar chromatographic surfaces, wherein the monolith has a surface morphology, as determined by scanning electron microscopy, that resembles the surface morphology of octadecyl modified poly(styrene-divinylbenzene) particles, wherein the surface morphology of the monolith is rugulose and brush-like, wherein the monolith is contained within a fused silica tube having an inner diameter in the range of 1 micrometer to 1000 micrometer, and wherein the monolith is immobilized at the inner wall of said tube. Preferred embodiments of this aspect of the invention can further include one or more of the following: the tube is devoid of retaining frits; the monolith is characterized by having 100,000 to 200,000 theoretical plates per meter; the monolith comprises an underivatized poly(styrene-divinylbenzene) matrix; and, the surface of said monolith is non-porous. The monolith can be formed from a polymerization mixture including underivatized styrene, a crosslinking agent, and a porogen, wherein the porogen comprises tetrahydrofuran. The polynucleotides can include double-stranded fragments having lengths in the range of 3 to 2000 base pairs, and preferably 3 to 600 base pairs.

In a final aspect, the invention concerns a chromatographic device. The device includes a polymeric monolith having non-polar chromatographic surfaces, wherein the monolith comprises an underivatized poly(styrene-divinylbenzene) matrix, wherein the monolith is characterized by having at least 10,000 theoretical plates per meter, wherein the monolith is contained within a silanized fused silica tube having an inner diameter in the range of 10 micrometer to 1000 micrometer, and wherein the monolith is immobilized at the inner wall of the tube. Preferred embodiments of this aspect of the invention can be further characterized by the following: the tube is devoid of retaining frits; the monolith is characterized by having 100,000 to 200,000 theoretical plates per meter; the monolith has a surface morphology, as determined by scanning electron microscopy, that resembles the surface morphology of octadecyl modified poly(styrene-divinylbenzene) particles, wherein the surface morphology of the monolith is rugulose; and wherein the monolith has a surface morphology, as determined by scanning electron microscopy, that resembles the surface morphology of octadecyl modified poly(styrene-divinylbenzene) particles, wherein the surface morphology of the monolith is brush-like. The monolith can be formed from a polymerization mixture including underivatized styrene, a crosslinking agent, and a porogen, wherein the porogen comprises tetrahydrofuran. The theoretical plates per meter preferably is determined from the retention time of single stranded $p(dT)_{18}$ standard using the following equation:

$$(N/L) = (5.54/L)\left(\frac{t_R}{w_{0.5}}\right)^2$$

wherein N is the number of theoretical plates, $t_R$ is the retention time of said standard determined during an isocratic elution, $w_{0.5}$ is the peak width at half height, and L is the length of the monolith in meters. During the isocratic elution the monolith preferably has a back pressure of 180 to 200 bar, and a flow rate in the range of 2 to 3 µL/min at an elution temperature of 50° C. Preferred embodiments of the device can be characterized by one or more of the following: the chromatographic surfaces of the monolith are non-porous; the monolith has channels sufficiently large for convective flow of said mobile phase; and, the monolith can be formed from a polymerization mixture including underivatized styrene, a crosslinking agent, and a porogen, wherein the porogen comprises tetrahydrofuran. The device can be used with back pressures in the range of about 20 to 300 bar, and with temperatures in the range of 20° C. to about 90° C.

DETAILED DESCRIPTION OF THE INVENTION

Figure 1A:
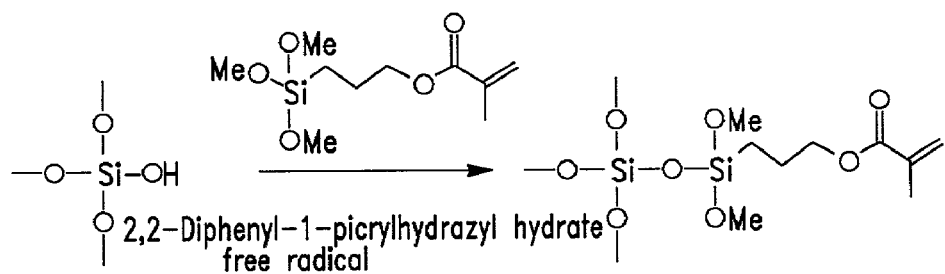
FIG. 1 illustrates a method for derivatization of a capillary silica wall by (a) vinyl-silanization and (b) subsequent grafting of the forming polymer.

The present invention generally relates to column chromatography. The chromatographic separation is carried out by forcing a liquid through a column packed with a monolithic matrix. A sample, such as a mixture of one or more polynucleotides, is introduced at the top of the column and then moves with the flow through the column. The polynucleotides are retarded on the matrix in such a manner that polynucleotides having different lengths are retarded differently during elution using a mobile phase gradient of organic solvent.

In its most general form, the invention concerns the separation of polynucleotides. e.g. DNA, utilizing a stationary separation medium having non-polar surfaces. The separation is performed on the stationary surface. Any surface micropores preferably are of a size which excludes the smallest polynucleotide being analyzed. In the invention, the separation surfaces comprise the surfaces of interstitial spaces in a molded polymeric monolith. The preferred separation medium is in the form of a polymeric monolith such as a monolithic rod. The monolith is polymerized or formed as a single unit inside of a tube. The channels (i.e., through-pores or macropores) provide for the passage of eluting solvent and analyte materials. The separation is performed on the stationary surface. All of the mobile phase is forced to flow through the channels of the separation medium (Petro et al. *J. Chromatogr. A* 752:59–66 (1996)). Without wishing to be bound by any particular theory, it is believed that mass transport is enhanced by such convection (Rodrigues et al. *J. Chromatogr.* 653:189 (1993); Liapis, *Math. Modelling Sci. Comput.* 1:397 (1993); Liapis et al. *J. Chromatogr. A* 660:85 (1994)) and has a positive effect on chromatographic efficiency (Afeyan et al. J. Chromatogr. 519:1–29 (1990)).

As used herein, the term "non-porous" is defined to include a monolithic separation surface which has surface micropores having a diameter that is less than the size and shape of the smallest polynucleotide fragment in the separation in the solvent medium used therein. Included in this definition are separation surfaces having these specified maximum size restrictions in their natural state or which have been treated to reduce their micropore size to meet the maximum effective micropore size required.

The surface conformations of monoliths of the present invention can include depressions and shallow pit-like structures which do not interfere with the separation process. A pretreatment of a porous monolith to render it non-porous can be effected with any material which will fill the micropores in the surface of the monolith structure and which does not significantly interfere with the IP-RP-HPLC process. "IP-RP-HPLC" includes a process for separating single and double-stranded polynucleotides using a non-polar separation medium, wherein the process uses a counterion agent, and an organic solvent to elute the nucleic acid from the non-polar surface of the medium.

As used herein, the term "polynucleotide" includes reference to a polymer of ribonucleic acid (RNA) or deoxyribonucleic acid (DNA), which can be single- or double-stranded, optionally incorporating synthetic, non-natural, or altered nucleotides capable of incorporation into DNA or RNA polymers, e.g., methylated nucleotides and nucleotide analogs. Polynucleotides may have any three-dimensional structure, and may optionally be partially or fully denatured. The following are non-limiting examples of polynucleotides: a gene or gene fragment (e.g., restriction fragments), exons, introns, messenger RNA, transfer RNA, ribosomal RNA, ribozymes, cDNA, recombinant polynucleotides, branched polynucleotides, plasmids, vectors, isolated DNA of any sequence, isolated RNA of any sequence, nucleic aid probes, and primers.

In a general aspect, the invention provides a chromatographic system for separating a mixture of polynucleotides. The system typically includes a separation column, a source of mobile phase, a pump, an injector, a column oven, a detector, a fraction collector, and a computer system including control software.

In a preferred embodiment of the instant invention, the chromatographic system utilizes miniaturized system components and column tubing having small inner diameters (e.g., having an ID of 1 micrometer to 5,000 micrometer, typically having and ID of 1 micrometer to 1,000 micrometer, and preferably having a column ID of about 10 micrometer to about 500 micrometer). Four major advantages connected with the use of smaller dimensions in chromatographic separation techniques can be specified: increased mass sensitivity with concentration-sensitive detectors allows the analysis of smaller samples (Novotny); on-line conjugation to mass spectrometry is feasible (Yergey et al. *Liquid Chromatography/Mass Spectrometry-Techniques and Applications,* Plenum Press, New York (1990); Niessen et al. *Liquid Chromatography-Mass Spectrometry: Principles and Applications,* Marcel Dekker, Inc., New York, (1992)); higher separation efficiency and better resolving power can be accomplished in shorter time (Karlsson et al. *Anal. Chem.* 60:1662–1665 (1988)); Kennedy et al. *Anal. Chem.* 61:1128–1135 (1989)); McCloskey in Mass Spectrometry, Academic Press Inc., San Diego (1990)); and expenses connected with consumption of mobile and stationary phase are cut down.

Without wishing to be bound by theory, high efficiency of microcolumns is attributed to decreased flow dispersion and a very homogenous packing bed structure, in which the stabilizing influence of the wall is felt by the entire packing bed (Kennedy). The volume of eluent used in microcolumn chromatography is considerably reduced, which means that the solutes of interest are dissolved in much less eluent, resulting in higher mass sensitivity and easier coupling with mass spectrometry.

In a preferred embodiment of the instant invention, microcolumn HPLC systems are designed and operated with the utmost attention to eliminating extracolumn band dispersion attributable to the sampling volume, detection volume, connecting tubing, and system time constant (Scott et al. *J. Chromatogr. Sci.* 20:62–66 (1982); Novotny *Anal. Chem.* 60:500A–510A (1988)). Introduction of small sample volumes and amounts into microcolumns by direct injection with microinjectors ($\leq 20$ nL), moving injection (Borra et al. *J. Chromatogr.* 395:75–85 (1987)), split injection (McGuffin et al. *Anal. Chem.* 55:580–583 (1983)), heart cutting injection (McGuffin et al.), or electrokinetic injection is mandatory for preventing column overloading and minimizing peak variance.

Also in a preferred embodiment of the present invention, the micro-HPLC detector is miniaturized in order to efficiently detect a narrow peak eluting from a capillary column. The detector is capable of monitoring the column effluent from capillaries with high fidelity. An example of a suitable detector is a curved capillary flow cell with improved performance for capillary HPLC (Chervet et al. *An Improved Method of and a Capillary Flow Cell for Analysing Fluid Samples,* European patent application no. 0597552A1 (1993)). In on-column detection, a section of the capillary column can be converted to the flow cell upon removing the polyimide coating and is exposed to the light beam of a conventional UV/VIS spectrophotometric detector (Chen et al. *Anal. Meth. Instr.,* 2:122–128 (1995)). Other detection methods and ancillary techniques can be used, such as conductivity, light scattering, evaporative detection, mass spectrometry (Yergey et al. (1990); Niessen et al. (1 992)), electrochemical detection (Colon et al. Anal. Chem. 65:476 (1993); Ewing et al. Anal. Chem. 66:527A (1994)), radiometric detection (Tracht et al. Anal. Chem. 66:2382 (1994)), and multichannel fluorescence detection (Timperman et al. Anal. Chem. 67:139 (1995)).

Because the gradient delay volume must be kept at a minimum, carrying out gradient elution in miniaturized HPLC is more complicated than using conventional solvent delivery systems. Some modifications of commercially available solvent delivery systems include stepwise gradients (Hirata et al. *J. Chromatogr.* 186:521–528 (1979)), split-flow operation (Van der Wal et al. *J. High Res. Chromatogr.* (1983); Chervet *Micro Flow Processor,* European patent application no. 0495255A1 (1991)), preformed gradients (Davis et al. *J. Am. Soc. Mass Spectrom.* 6:571–577 (1995)), and miniaturized diluting chambers (Takeuchi et al. *J. Chromatogr.* 253:41–47 (1982); Karlsson et al. *J. Chromatogr.* 7:411–413 (1984)). Commercially available micro-HPLC instrumentation with micro-mixing chambers is capable of performing reproducible gradients with flow rates as low as 5–10 µL/min without solvent splitting.

High pressure pumps are used for pumping mobile phase in the systems described herein. It will be appreciated that other methods are known for driving mobile phase through separation media and can be used in carrying out the separations of polynucleotides as described in the present invention. A non-limiting example of such an alternative method includes "capillary electrochromatography" (CEC) in which an electric field is applied across capillary columns packed with microparticles and the resulting electroosmotic flow acts as a pump for chromatography. Electroosmosis is the flow of liquid, in contact with a solid surface, under the influence of a tangentially applied electric field. The technique combines the advantages of the high efficiency obtained with capillary electrophoretic separations, such as capillary zone electrophoresis, and the general applicability of HPLC. CEC has the capability to drive the mobile phase through columns packed with chromatographic particles, especially small particles, when using electroosmotic flow. High efficiencies can be obtained as a result of the plug-like flow profile. In the use of CEC in the present invention, solvent gradients are used and rapid separations can be obtained using high electric fields. The following references describing CEC are each incorporated in their entirety herein: Dadoo, et al, *LC-GC* 15:630 (1997); Jorgenson, et al., *J. Chromatog.* 218:209 (1981); Pretorius, et al., *J. Chromatog.* 99:23 (1974); and the following U.S. Pat. Nos. to Dadoo U.S. Pat. No. 5,378,334 (1995), U.S. Pat. No. 5,342,492 (1994), and U.S. Pat. No. 5,310,463 (1994). Another example of a method for driving mobile phase includes centrifugal force, such as described in U.S. Pat. No. 6,063,589.

In a particular aspect, the instant invention provides a separation column that consists of a polymeric monolith having non-polar chromatographic surfaces. The process for producing the columns generally comprises (1) adding to a rigid tube sealed at both ends a deaerated polymerizable mixture containing an inert porogen; (2) polymerizing the mixture, typically in the presence of a catalyst, to form a macroporous polymer plug; and (3) washing the plug with a solvent so as to remove the porogen present in the macroporous polymer produced. The polymerizable mixture contains a suitable monomer or monomer mixture with appropriate amounts of a suitable crosslinker.

Macroporous matrices are obtained when polymerization and crosslinking take place in the presence of inert porogens which lead to a phase separation during the ongoing polymerization reaction and effect the formation of permanent channels in the material (Seidl et al. *Adv. Polymer Sci.*, 5:113–213 (1967); Hjerten et al. *Nature*, 356:810–811 (1992); C. Viklund et al. *Chem. Mater.* 8:744–750 (1996)). The concept of monolithic stationary phases is especially favorable for the fabrication of capillary columns.

Applicants have found that the exact adjustment of the polymerization conditions is crucial for the preparation of high performance monoliths of the present invention. These conditions include use of an inert component, the porogen, or a mixture of such inert components that do not participate in the polymerization and which are soluble in or at least miscible with the monomer. Careful control of the polymerization kinetics is also required to model the morphology of the formed polymer. Temperature, reaction time, concentration of radical initiator, ratio of monomer to crosslinker affect the performance of the monolith.

The most important parameters for the construction of special channel sizes are monomer type and reactivity, degree of crosslinking, amount and type of porogen(s), solvency of the porogen(s) for the polymer, and polymerization temperature (Seidl et al.; Svec et al. *Macromolecules* 28:7580–7582 (1995); Viklund et al. *Chem. Mater.* 9:463–471 (1997); Wang et al. *Anal. Chem.* 64:1232–1238 (1992)). To avoid undesired sedimentation, the columns can be rotated slowly in the course of the polymerization process. Column permeability and performance can be modulated over a wide range by varying the amount of porogen in the polymerization mixture. For differing compositions of the porogen, the amount of radical initiator has to be newly optimized to maintain a reasonable separation performance. Monoliths with high back pressure can be obtained using high percentages of porogen, while for columns with lower back pressure a composition with high amount of initiator and a low percentage of the porogen tetrahydrofuran is preferred. Additionally, not all the pieces that are cut from one synthesized capillary monolithic column are identical and the chromatographic performance of the pieces must be determined The preferred monolithic columns were synthesized to exhibit hydrodynamic properties comparable to that of packed columns. The back pressure in a 6 cm long monolithic column (prepared as described in Example 3) for water at a flow rate of 3 μL/min is was in the range of 90 to 120 bar, which compares well to a column packed with non-porous beads of equal dimensions and comparable chromatographic efficiency that exhibited a back pressure of 150 bar. The lower back pressure in monoliths is a result of increased macroporosity. The monoliths of the invention can be used at back pressures in the range of about 20 to 300 bar. The back pressure will be dependant upon the dimensions, the length and inner diameter, of the tube. In general, a shorter tube will give a lower back pressure.

The method preferably is performed at an elution temperature within the range of 20° C. to 90° C.

In an important aspect, the instant invention is based on the surprising and unexpected discovery that an underivatized poly(styrene-divinylbenzene) (PS-DVB) monolith exhibited highly efficient separation performance. This was unexpected, since the disclosure in the published patent application WO 00/15778, which further cited other suggestions in the literature, disclosed that underivatized poly (polystyrene/divinlybenzene) structures are not desirable for DNA separations. It was disclosed that no useful separation using such monoliths were obtained. In the present invention, the term "underivatized", as used in describing a monolithic matrix, is used herein to indicate that the monolithic matrix is not subsituted with alkyl moieties (such as straight chain, branched or aromatic hydrocarbons) or with non-alkly moieties (such as charged or polar groups).

In preparing the monoliths of the present invention, a preferred monomer is styrene and a preferred crosslinking agent is divinylbenzene. Examples of preferred porogens include toluene, decanol, hexane and tetrehydrofuran.

Based on preliminary experiments, a ratio of monomer to porogen mixture of 2:3 was found suitable in the preparation of the monoliths of the present invention. The chemical purity of the commercially available styrene was better than 99%. However, an assay of the utilized divinylbenzene revealed that only 65% of the used reagent were indeed isomers of divinylbenzene, capable of performing the crosslinking of polymer chains, while a percentage of about 33% was formed by different ethylvinyl benzenes that can act as a monomer for polymerization, but not crosslinker. In the description herein, the true amount or percentage of chemically pure divinylbenzene is indicated, and the amount or percentage of the non crosslinking ethylvinyl benzene was added to that of styrene. The composition of mixtures is either given in absolute masses or as percentages weight-per-weight. The density of the most used reagents is given in Table 1.

TABLE 1

Density of the components of the polymerization mixture

| component | density $\rho_{20° C.}$ [kg/m$^3$] |
|---|---|
| styrene | 909 |
| divinylbenzene | 914 |
| 1-decanol | 829 |
| hexane | 660 |
| tetrahydrofuran | 889 |
| toluene | 867 |

In a preferred embodiment of the instant invention, the monolith is comprised of an underivatized poly(styrene-divinylbenzene) matrix. Applicants have surprisingly discovered that the porogenic solvent tetrahydrofuran gave monolithic columns displaying unexpectedly high efficiency of separation of polynucleotides. Therefore, a preferred porogenic solvent includes tetrahydrofuran. A more preferred porogen solvent comprises a mixture of tetrahydrofuran and decanol.

An embodiment of a polymerization mixture for the synthesis of suitable columns for the separation of biopolymers included the following: 0.5948 g non-crosslinking monomer (styrene+ethylvinyl benzene), 0.2911 g crosslinker (divinylbenzene), 1.0062 g 1-decanol, 0.1759 g tetrahydrofuran, and 0.0193 g α,α'-azobisisobutyronitrile (ABIN). Monolithic capillary columns were produced by polymerization at 70° C. for 24 hours.

Without wishing to be bound by theory, it is believed that the improved separation performance of the monolithic columns of the instant invention is due to the use of tetrahydrofuran as microporgen, which is more polar and of poorer solvency for the polymer than the commonly used toluene. The resulting polymer contains relatively large channels that allow rapid convective mass transport between the mobile phase and a thin out layer of the polymer. This configuration adequately imitates the configuration of micropellicular, beaded stationary phases (e.g., as disclosed in U.S. Pat. No. 5,585,236), which have been shown to be highly suitable for high-speed separations of biopolymers.

Figure 1B:
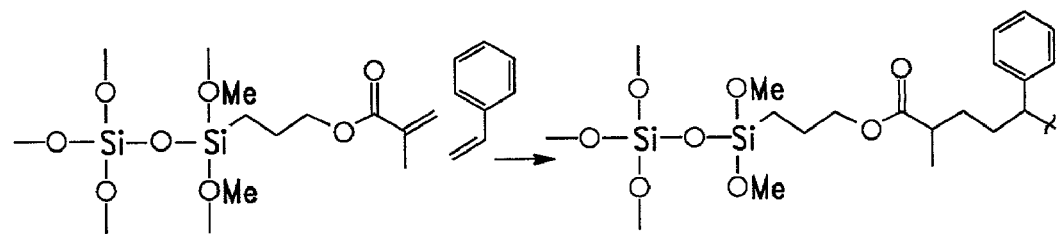

In another aspect, the instant invention provides a monolith that is contained within a tube and which is immobilized at the inner wall of the tube. In a preferred embodiment, the monolith is immobilized by covalent attachment at the inner wall of the tube. Shrinking of the monolith can be an issue during polymerization. The overall volume shrinkage during polymerization of methacrylate polymers amounts to approximately 6%, and shrinkage occurs mainly at a late point in polymerization within the formed and already crosslinked monolith (Brooks *Macromol. Chem., Macromol. Symp.* 35/36:121 (1990)). Therefore an extension of the channels is to be expected rather than a shrinkage of the exterior dimensions and detaching from the capillary wall. Furthermore, derivatization of the capillary inner wall with vinylsilanes facilitates wetting with polymerization mixture, reduces the formation of bubbles and can be used to chemically attach the formed polymer to the silica surface. A representative example of a process for covalent attachment is shown in FIG. 1 and as described in Example 2.

Monoliths that were prepared without previous vinylsilylation, and thus without anchoring to the inner capillary wall, underwent compression when subjected to high pressures from a HPLC pump. A monolith was prepared by allowing to react a mixture of 0.40 mL styrene, 1.80 mL divinylbenzene, 50 mg AIBN, 2.25 mL 1-decanol and 0.75 mL toluene at 70° C. for 14 hours within a 200×0.32 mm fused silica capillary. Acetonitrile was pumped through an 80 mm long piece of this capillary and the monolith was held in its place by a PEEK frit in a stainless steel union. A longitudinal compression of 2 mm out of 80 mm , corresponding to a reduction of length of 2.5%, was observed when a pressure of 200 bar was applied. The pressure-to-flow curve starts out linearly, but begins to rise exponentially as soon as compression of the monolith and thus restriction of the channels begins at a flow rate of 6 μL/min and a respective back pressure of 25 bar (data not shown). No such compression was observed and a linear pressure-to-flow curve over the whole range of tested flow rates and applied pressure was observed with monoliths that were chemically immobilized to the surface.

The monolithic columns prepared as described herein can be equipped with conventional retaining frits. However, in preferred embodiments, the monolithic columns of the invention are devoid of retaining frits. Thus in another aspect, the invention provides a polymeric monolith, preferably an underivatized poly(styrene-divinylbenzene) monolith, that is contained within a tube wherein the tube is devoid of retaining frits. In preferred embodiments, the monolith is immobilized at the capillary wall during polymerization. Such immobilization eliminates the necessity to prepare a tiny retaining frit, which is one of the more tedious and difficult to control steps during the manufacture of packed bed capillary columns (Svec et al. *Macromolecules* 28:7580–7582 (1995); C. Ericson et al. *J. Chromatogr. A* 767:33–41 (1997); Oberacher et al. *J. Chromatogr. A* 893: 23–35 (2000)). Capillary columns prepared without frits are thus easier to prepare and less expensive.

After polymerization is complete, the solid monolith is preferably washed to remove any porogenic solvent and with a suitable solvent to dissolve any soluble polymer present. Suitable washing solvents include methanol, ethanol, benzene, acetonitrile, toluene acetone, tetrahydrofuran, and dioxane. This washing process may be done in stages; for example by alternatively washing with solvent and water, or by continuous washing with a solvent. The washing step is performed by pumping the solvent through the tube filled with the monolith.

A wide variety of conventional support structures, such as a tube, a channel or groove on a plate, a thin film across a plate, or a microchip, can be used with the monolithic matrix of the instant invention. Examples of such structures are described, for example, in WO 00/15778.

A still further aspect of the instant invention concerns the morphology of the surface structure of the monolith. The morphology of the synthesized monolithic polymers was optically characterized by light microscopy and by scanning electron microscopy. The homogeneity of the monolithic stationary phase over the length of the capillary was controlled using an Olympus BH-2 light microscope (magnification factor from 40 to 1,000). Electron micrographs were acquired using a Voyager ARL-SEMQ-electron micrograph (Noran Instruments Inc., Middleton, Wis.) with a magnification factor from 200 to 30,000.

Figure 9:
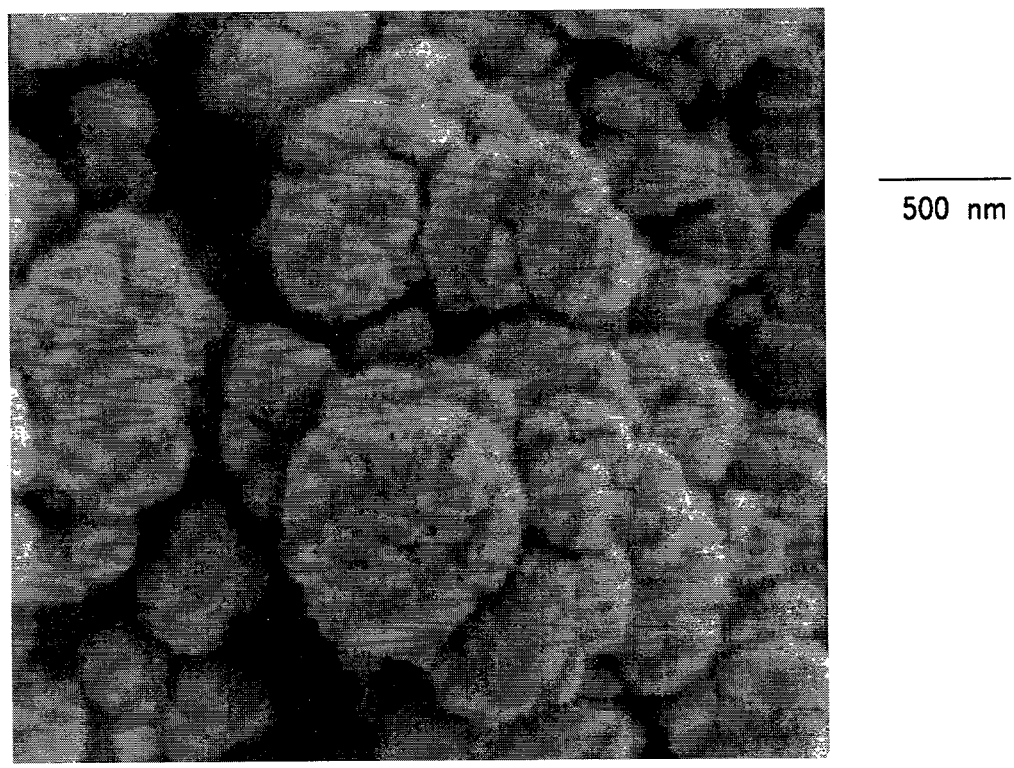
FIG. 9 shows a scanning electron micrograph of an underivatized PS-DVB monolith.

Scanning electron micrographs were acquired to characterize the column morphology and surface structure. FIG. 9 shows scanning electron micrographs of the stationary phase made of a highly crosslinked, underivatized, styrene-divinylbenzene copolymer monolith. The cross section of the rod reveals clusters of globules separated by large channels. The average size of the globules is in the range of 100 to 200 nm, they form the building units for larger aggregates with a diameter from 500 to 800 nm. The size of the channels between the clusters reaches 500 nm, corresponding well to those measured by inverse size exclusion chromatography.

The surface structure of the poly(styrene-divinylbenzene) monoliths of the present invention was compared to that of octadecyl modified poly(styrene-divinylbenzene) particles, which have been shown to be highly suitable for high-speed separation of polynucleotides (Huber et al. *Anal. Biochem.* 212:351–358 (1993); U.S. Pat. No. 5,585,236). The monolith was observed to have relatively large channels. Without wishing to be bound by theory, these channels are thought to allow rapid convective mass transport between the mobile phase and a thin outer layer of the polymer.

Figure 7:
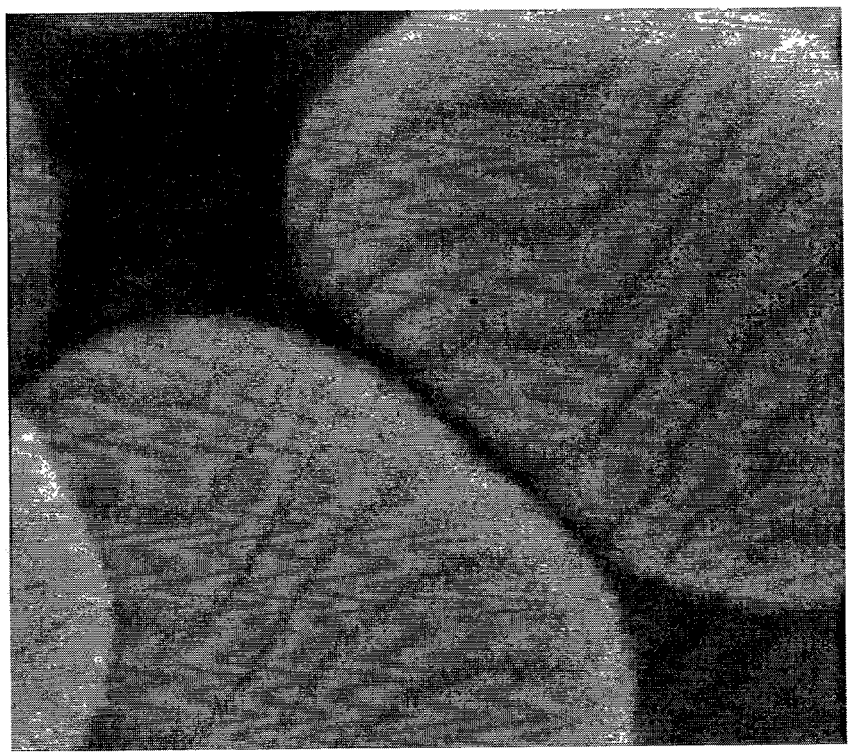
FIG. 7 shows a scanning electron micrograph of underivatized PS-DVB particles.
Figure 8:
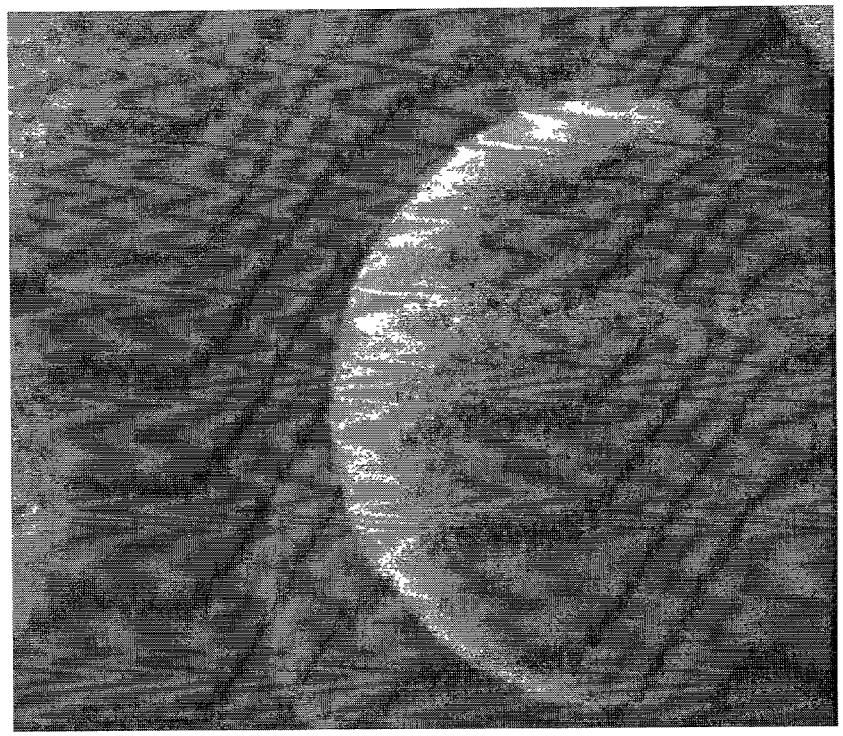
FIG. 8 shows a scanning electron micrograph of octadecylated PS-DVB particles.

Applicants surprisingly discovered that the surface structure of the underivatized poly(styrene-divinylbenzene) monoliths resembled the surface structure of the octadecyl derivatized beads, both showing a surface that appeared rugulose, but not the underivatized beads, which showed a smooth surface. While derivatization with octadecyl groups has been shown to be essential to obtain high chromatographic efficiency with PS-DVB particles (Huber et al. *Anal. Biochem.* 212:351–358 (1993); Huber et al. *Nucleic Acids Res.* 21:1061–1066 (1993)) monolithic stationary phases exhibited superior efficiency already without derivatization. Without wishing to be bound by theory, one possible explanation for this different behavior is the formation of the polymer in two different chemical environments. The PS-DVB particles were polymerized in aqueous suspension, where poor solvation of the hydrophobic polymer by the hydrophilic solvent resulted in a relatively flat surface, as revealed by the scanning electron micrograph depicted in FIG. 7. Particles that were derivatized with octadecyl groups showed a rugulose surface (FIG. 8) possibly offering a contact area greater than that of a smooth spherical particle. The formation of the monolithic bed, on the other hand, took place in an entirely organic environment. During polymerization, small primary particles of approximately 0.5 μm coagulated to form the porous monolith, resulting in a surface structure (FIG. 9) that resembled the rugulose surface of the octadecylated PS-DVB particles (FIG. 8). Without wishing to be bound by theory, Applicants believe that the very rugulose surface of the stationary phase of the monolith of the present invention offers a contact area greater than that of smooth spherical particles and that this enhanced contact area gives improved separation performance. A "rugulose surface" as defined herein includes a surface characterized by showing many small wrinkles. It was also observed that a particle that was derivatized with ocatadecyl groups had a brush-like surface (FIG. 8). A "brush-like surface" as defined herein includes a surface characterized by showing many small bristles on the surface. The monolith (FIG. 9) also had a brush-like surface structure, unlike the underivatized particle (FIG. 7).

In still another aspect, the poly(styrene-divinylbenzene) monolith of the present invention provides a non-porous chromatographic surface. With a gradient of 4.0–12.0% acetonitrile in 50 mM TEAA in 10 min, oligothymidylic acids as small as the 3-mer were eluted as sharp and symmetric peaks (chromatogram not shown). From the crystal structure of the trinucleotide $(A)_3$ it can be inferred, that a 3-mer oligodeoxynucleotide has an almost globular structure with a diameter of approximately 1.0 nm (Suck et al. *Acta Crystallogr., Sect.* B 32:1727–1737 (1976)). Because penetration of analytes into micropores of commensurate size would cause considerable band broadening, the capability of the monolithic stationary phase to efficiently separate such small molecules is a good indicator for the absence of micropores.

A still further aspect of the present invention is based on the surprising discovery that the underivatized poly(styrene-divinylbenzene) monoliths having nonpolar chromatographic surfaces were found to provide unusually high efficiency of separation of polynucleotides. In this aspect, the invention provides a monolith characterized by having high separation efficiency as indicated by a high number of theoretical plates per meter. Two terms are widely used as quantitative measures of band spreading and thus chromatographic column efficiency: the plate height H and the number of theoretical plates N. The two parameters are related by the equation:

$$N=L/H \qquad (1)$$

The plate height and the dimensionless number of theoretical plates express the peak variance per unit length of the column and the dimensionless peak variance, respectively (Poole et al. *Chromatography Today,* Elsevier, Amsterdam (1995); *Practical HPLC Method Development* Snyder et al. Eds., John Wiley & Sons, New York, pp. 40–47 (1997)). Assuming that the form of the chromatographic peak can be approximated by a Gaussian curve, the number of theoretical plates can experimentally be determined from the equation:

$$N = 5.54\left(\frac{t_R}{w_{0.5}}\right)^2 \qquad (2)$$

$t_R$ . . . retention time [sec]

$w_{0.5}$ . . . peak width at half height [sec]

The number of theoretical plates and the plate height are widely used in the art as measures of column performance. For these numbers to be meaningful in comparing two columns, it is essential that they are determined with the same compound and under the same isocratic elution conditions.

In a preferred embodiment of this aspect of the present invention, calculation of the number of theoretical plates is based on the retention time of a single polynucleotide standard under isocratic conditions. A preferred standard comprises a single-stranded oligodeoxynucleotide. In one example, the single-stranded polynucleotide, poly$(dT)_{18}$ was used as a standard for the determination of the number of theoretical plates per meter. The chromatographic efficiency of the monolithic columns was determined by isocratic elution of poly$(dT)_{18}$ with a mobile phase containing 7.8% acetonitrile in 100 mM TEM at a flow rate of 2.4 μL/min. At 50° C. column temperature, the number of theoretical plates exceeded 11,500 plates for a 60 mm column, corresponding to (N/L)=191,000 theoretical plates per meter.

The capillary monolithic column of the present invention is characterized by having in the range of between about 10,000 and about 200,000 theoretical plates per meter, preferably between 100,000 and 200,000 theoretical plates per meter, more preferably at least 100,000 plates per meter, and most preferably at least 190,000 theoretical plates per meter. Without wishing to be bound by theory, it is believed that one of the main reasons for the high separation efficiency of the monoliths is the rapid mass transfer with the only particle-based diffusion limitation in a thin layer at the surface of monolith.

In another aspect, the invention provides a method for separating a mixture of polynucleotides in which the method includes applying the mixture of polynucleotides to a polymeric monolith, such as an underivatized poly(sytrene-divinylbenzene) monolith, having non-polar chromatographic surfaces and eluting the mixture of polynucleotides with a mobile phase comprising a counterion agent and an organic solvent. When analyzing double-stranded polynucleotides, the method can be used to analyze polynucleotides having a wide range of lengths. For example, the method can be used in analyzing polynucleotides having lengths in the range of about 3 base pairs to about 600 base pairs. The method can also be used in analyzing polynucleotides having up to about 2,000 base pairs. The elution step preferably uses a mobile phase containing a counterion agent and a water-soluble organic solvent. Examples of a suitable organic solvent include alcohol, acetonitrile, dimethylformamide, tetrahydrofuran, ester, ether, and mixtures of one or more thereof, e.g., methanol, ethanol, 2-propanol, 1-propanol, tetrahydrofuran, ethyl acetate, acetonitrile. The counterion agent is preferably selected from the group consisting of lower alkyl primary amine, lower alkyl secondary amine, lower alkyl tertiary amine, lower trialkyammonium salt, quaternary ammonium salt, and mixtures of one or more thereof. Examples of suitable counterion agents include triethylammonium acetate (TEM) and triethylammonium bicarbonate (TEAB).

In an additional aspect, the invention provides a method for separating a mixture of polynucleotides in which the method includes applying the mixture of polynucleotides to a poly(styrene-divinylbenzene) monolith, such as underivatized poly(styrene-divinylbenzene), having non-polar chromatographic surfaces and eluting the mixture of polynucleotides with a mobile phase comprising a counterion agent and an organic solvent, wherein the mobile phase is devoid of metal chelating agent, such as EDTA. The elutions described in the Examples herein are performed using mobile phase lacking EDTA. Avoiding the use of EDTA is an advantage since EDTA in eluted fractions can interfere with subsequent mass spectral analysis. Removal of EDTA would require additional processing steps.

In a still further aspect, the invention concerns a method for separating a mixture of polynucleotides in which the method includes applying the mixture of polynucleotides to a poly(styrene-divinylbenzene) monolith having non-polar chromatographic surfaces and eluting the mixture of polynucleotides with a mobile phase comprising a counterion agent and an organic solvent, in which the method further includes analyzing the eluted polynucleotides by mass spectral analysis. The monolithic column can be operatively coupled to a mass spectrometer for determining the molecular mass of the eluted polynucleotides. In a preferred embodiment, the mass spectrometer comprises an electrospray ionization (ESI) mass spectrometer. The electrospray ionization mass spectrometer can include a tandem mass spectrometer for determining the base sequences of the polynucleotides.

The possibility of direct on-line conjugation of capillary HPLC to mass spectrometry makes available highly valuable information about the structure and identity of the separated compounds (Tomer et al. *Mass Spectrom. Rev.* 13:431–457 (1994)). Electrospray ionization mass spectrometry (ESI-MS), by virtue of the multiple charging of biopolymers and the very soft ionization process, has become one of the most important mass spectrometric techniques for the analysis of nucleic acids (Nordhoff et al. P. *Mass Spectrom. Rev.* 15:76–138 (1996)). Nevertheless, the success of ESI-MS for the characterization of nucleic acids largely depends on the purity of the sample that is introduced into the mass spectrometer (Portier et al. *Nucleic Acids Res.* 22:3895–3903 (1994)). The major difficulties arise due to the tendency of nucleic acids to form quite stable adducts with cations resulting in mass spectra of poor quality (Stults et al. *Rapid Commun. Mass Spectrom.* 5:359–363 (1991); Huber et al. *Anal. Chem.* 70:5288–5295 (1998)). As described hereinbelow, Applicants have observed that the on-line sample preparation of polynucleotides by chromatographic separation prior to ESI-MS removes cations from nucleic acid samples, and can be used to fractionate the polynucleotides in mixtures that are too complex for direct infusion ESI-MS.

The potential to obtain high quality ESI-mass spectra of large, double-stranded DNA is essentially determined by the amount of salt as well as the number of different compounds present in the sample mixture (Portier et al. *Nucleic Acids Res.* 22:3895–3903 (1994); Muddiman et al. *Anal. Chem.* 68:3705–3712 (1996)). Recently, Muddiman et. al. published the mass spectrum of a 500 bp polymerase chain reaction product, which has been purified by ethanol precipitation followed by microdialysis (Muddiman et al. *Rapid Commun. Mass Spectrom.* 13:1201–1204 (1999)). Although the amount of DNA that was analyzed in the ion cyclotron resonance mass spectrometer was in the low femtomol range, much more material was required for purification before mass measurement. Hence, there is an urgent need for rapid on-line separation and purification protocols requiring only minute sample amounts.

In a yet further aspect, the present invention provides a method for desalting and separating a mixture of single-stranded polynucleotides. The method includes dissolving a mixture of single-stranded polynucleotides in a mobile phase having a lower concentration of organic solvent than an initial mobile phase composition. The method further includes loading the mixture onto a poly(styrene-divinyl-benzene) monlithic column, as described herein, and flowing initial mobile phase containing a counterion agent and having a concentration of organic solvent that is below the level that would elute the polynucleotides through the column such that the polynucleotides are retained and the salts are removed from the polynucleotides. The method further includes separating the mixture of polynucleotides by eluting the mixture of polynucleotides with a mobile phase comprising a counterion agent and an organic solvent. This desalting method preferably includes preconcentrating the polynucleotides on the monolithic column. The volume loading capacity describes the maximum injection volume at constant analyte amount that can be loaded onto a separation column without the occurrence of peak broadening. Analytes which are present in extremely low concentrations in the sample may necessitate the injection of large sample volumes. Biomolecules exhibit very steep capacity curves in the reversed-phase mode and react very sensitive to small changes in mobile phase composition. Hence, a preconcentration at the column head occurs and injection of large volumes of sample containing a low concentration of analyte is possible without deleterious effects on the separation efficiency.

Monolithic capillary columns as described herein have numerous advantages when used in the separation of polynucleotides. The preparation can be carried out following simple procedures and an improved chromatographic separation performance can be obtained. Specific advantages include:

The small volumes and low amounts of samples available from biochemical, medical or molecular biological experiments are most adequately processed by micro separation techniques.

Polymerization within the confines of fused silica capillaries of small inner diameter is a straightforward way to manufacture monolithic columns for capillary and nano HPLC.

By anchoring the chromatographic support material to the capillary wall using covalent chemical bonding, no tedious preparation of frits is necessary. Moreover, there is no need to pack columns using high pressure devices and no restrictions in achievable capillary length apply.

The permeability of the monolithic capillary columns can be modulated by choosing an appropriate polymerization mixture. Columns with high permeability exhibit a lower back pressure than packed capillary columns and greater capillary lengths are possible for chromatographic separations.

The enhanced mass transport through continuous macroporous polymer has a positive effect on chromatographic efficiency.

Expenses connected with consumption and disposal of materials are cut down.

The low flow rates applied in microcolumn high performance liquid chromatography are ideally suited for on-line coupling with electrospray ionization mass spectrometry.

Other features of the invention will become apparent in the course of the following descriptions of exemplary embodiments which are given for illustration of the invention and are not intended to be limiting thereof.

Procedures described in the past tense in the Examples below have been carried out in the laboratory. Procedures described in the present tense have not yet been carried out in the laboratory, and are constructively reduced to practice with the filing of this application.

EXAMPLE 1

Chemicals and Oligodeoxynucleotide Samples

Acetonitrile (HPLC gradient-grade), divinylbenzene (synthesis grade), methanol (HPLC gradient-grade), styrene (synthesis grade), and tetrahydrofuran (analytical reagent grade) were obtained from Merck (Darmstadt, Germany). Styrene and divinylbenzene were distilled before use. Acetic acid (analytical reagent grade), azobisisobutyronitrile (synthesis grade), decanol (synthesis grade), and triethylamine (p.a.) were purchased from Fluka (Buchs, Switzerland). A 1.0 M stock solution of triethylammonium acetate (TEM) was prepared by dissolving equimolar amounts of triethylamine and acetic acid in water. A 0.50 M stock solution of triethylammonium bicarbonate (TEAB) was prepared by passing carbon dioxide gas (AGA, Vienna, Austria) through a 0.50 M aqueous solution of triethylamine at 5° C. until pH 8.4–8.9 was reached. For preparation of all aqueous solutions, high-purity water (Epure, Barnstead Co., Newton, Mass., USA) was used. The standards of phosphorylated and non-phosphorylated oligodeoxynucleotides ($(dT)_{12-18}$, $p(dT)_{12-18}$, $p(dT)_{19-24}$, $p(dT)_{25-30}$) were purchased as sodium salts from Pharmacia (Uppsala, Sweden) or Sigma-Aldrich (St. Louis, Mo., USA). The synthetic oligodeoxynucleotides $(dT)_{24}$ ($M_r$ 7,238.71), a 5'-dimethoxytritylated 5-mer (DMTr-ATGCG, $M_r$ 1805.42), and an 80-mer ($M_r$ 24,527.17):

```
CCCCAGTGCTGCAATGATACCGCGAGACCCACGCTCACCGGCTCCAGATTTAT    (SEQ ID NO:1)

CAGCAATAAACCAGCCAGCCGGAAGGG
``` were ordered from Microsynth (Balgach, Switzerland) and used without further purification. The size standard of double-stranded DNA restriction fragments (pBR322 DNA-Hae III digest) was purchased from Sigma Aldrich.

EXAMPLE 2

Preparation of Fused Silica Capillaries

Fused silica capillaries with an inner diameter of 200 μm and a length of 3 m were flushed with 2 mL of methanol and 2 mL of water, filled with 1 mol/L sodium hydroxide, closed at the ends and allowed to stand for 10 min at room temperature. Subsequently, the capillary was washed with 2 mL of water and 2 mL of methanol, and dried with nitrogen for 15 min at room temperature. Before in situ polymerization the inner wall of the fused silica tube was silanized in order to facilitate wetting by the solution of the monomer mixture and to allow covalent immobilization of the monolith in the tube (FIG. 1). By attaching the bed to the tubing wall, gap formation between the capillary wall and the polymer due to shrinking of the polymer upon a change of solvent is avoided and no frit to support the bed is required.

In the silanization process, a mixture of 50% (v/v) 3-(trimethoxysilyl)propyl methacrylate and 0.01% (w/v) 2,2-diphenyl-1-picrylhydrazyl hydrate in dimethylformamide (DMF) was degassed with nitrogen for 5 min and filled into a pretreated, 3 m piece of fused silica capillary tubing (Huang et al. J. Chromatogr. A 788:155–164 (1997)). The ends of the tubing were closed with silicon stoppers and the capillary was kept in an oven at 120° C. for six hours. Next the capillary was flushed with 2 mL each of DMF, methanol and dichloromethane, and finally dried with nitrogen.

EXAMPLE 3

Preparation of Continuous-bed and Packed-bed Capillary Columns

Polyimide coated fused silica capillary tubing of 350 μm OD and 200 μm ID was obtained from Polymicro Technologies (Phoenix, Ariz., USA). A 1 m piece of fused silica capillary tubing was silanized with 3-(trimethoxysilyl)propyl methacrylate (Huang et al. C. J. Chromatogr. A 788: 155–164 (1997)) in order to ensure immobilization of the monolith at the capillary wall. Then, a 300 mm piece of the silanized capillary was filled with a mixture comprising 50 μL styrene, 50 μL divinylbenzene, 130 μL decanol, 20 μL tetrahydrofuran, and 10 mg/mL azobisisobutyronitrile with a plastic syringe. The mixture was polymerized at 70° C. for 24 hours. After polymerization, the capillary was extensively flushed with acetonitrile at a flow rate of 5.0 μL/min and finally cut into 60 mm long pieces. Octadecylated PS-DVB particles (PS-DVB-$C_{18}$) were synthesized as published in the literature (Huber et al. Anal. Biochem. 212: 351–358 (1993)). The PS-DVB-$C_{18}$ stationary phase has been commercialized as DNASep® columns by Transgenomic Inc. (San Jose, Calif., USA). Packed-bed capillary columns were prepared according to the procedure described (Oberacher et al. J. Chromatogr. A (2000)).

EXAMPLE 4

High-performance Liquid Chromatography

The HPLC system consisted of a low-pressure gradient micro pump (model Rheos 2000, Flux Instruments, Karlskoga, Sweden) controlled by a personal computer, a vacuum degasser (Knauer, Berlin, Germany), a column thermostat made from 3.3 mm OD copper tubing which was heated by means of a circulating water bath (model K 20 KP, Lauda, Lauda-Königshofen, Germany), a microinjector (model C4-1004, Valco Instruments Co. Inc., Houston, Tex., USA) with a 200 or 500 nL internal sample loop, a variable wavelength detector (model UltiMate UV detector, LC Packings, Amsterdam, Netherlands) with a Z-shaped capillary detector cell (part no. ULT-UC-N-10, 3 nL cell, LC Packings), and a PC-based data system (Chromeleon 4.30, Dionex-Softron, Germering, Germany).

EXAMPLE 5

Figure 2:
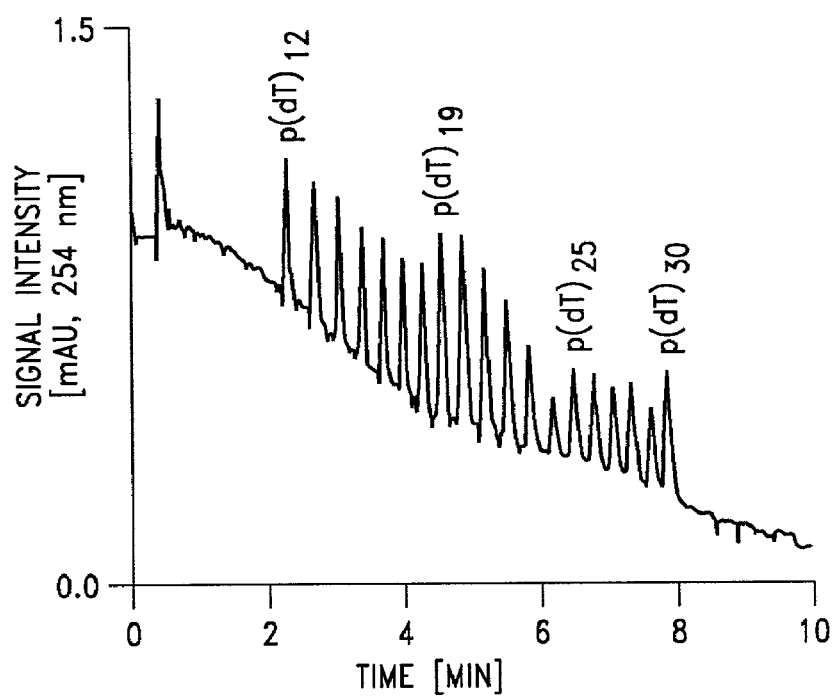
FIG. 2 is a chromatogram showing capillary ion-pair reverse phase-high pressured liquid chromatography (IP- RP-HPLC) separation of phosphorylated polynucleotide ladders (0.66–1.64 fmol of each polynucleotide) in a monolithic capillary column constructed in accordance with an embodiment of the present invention.

High-resolution Capillary IP-RP-HPLC Separation of Phosphorylated Oligodeoxynucleotide Ladders in a Monolithic Capillary Column Using the column as described in Example 3, a high-resolution capillary IP-RP-HPLC separation of a phosphorylated oligodeoxynucleotide ladder was performed (FIG. 2): Column, continuous PS-DVB, 80×0.20 mm ID; mobile phase, buffer A 100 mM TEAA, pH 6.80, buffer B 100 mM TEAA, pH 6.80, 20% acetonitrile; linear gradient, 32–42% B in 3.0 min, 42–52% B in 7 min;flow-rate, 3.3 μL/min; temperature, 50° C.; detection, UV, 254 nm; sample, p(dT)$_{12-30}$, 6 ngram each/0.66–1.64 pmol each.

EXAMPLE 6

Separation of Phosphorylated Oligodeoxyadenylic- and Oligothymidylic Acids

Figure 3:
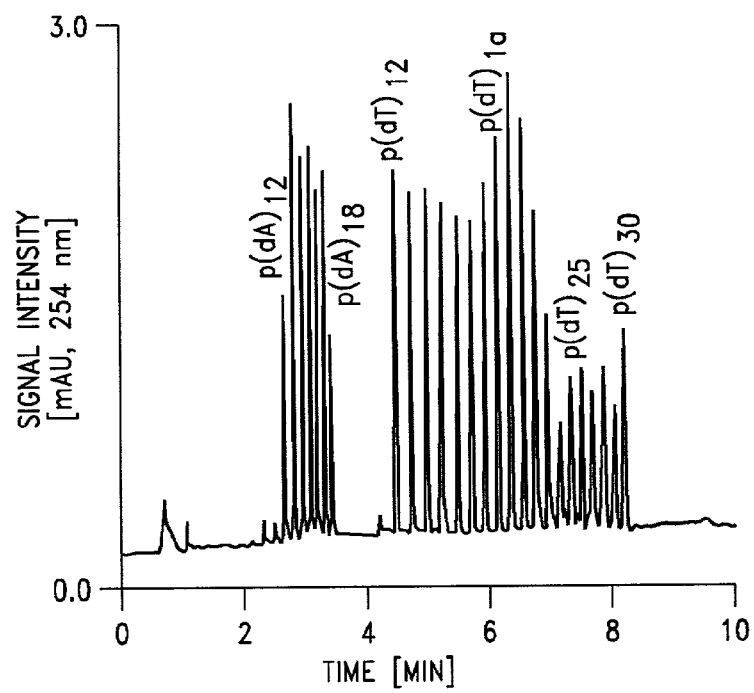
FIG. 3 is a chromatogram showing capillary ion-pair reverse phase-high pressured liquid chromatography (IP-RP-HPLC) separation of phosphorylated polynucleotide ladders (40–98 fmol of each polynucleotide) in a monolithic capillary column constructed in accordance with an embodiment of the present invention.

FIG. 3 illustrates the high-resolution separation of phosphorylated oligodeoxyadenylic- and oligothymidylic acids ranging in size from 12–30 nt. Gradient elution with 3.0–9.0% acetonitrile in 3.5 min, followed by 9.0–11.0% acetonitrile in 2.5, and finally 11.0–13.0% acetonitrile in 4.0 min in 100 mM TEAA resulted in peak widths at half height of 1.3 s for $p(dA)_{12}$ to 2.4 s for $p(dT)_{30}$ which allowed the baseline resolution of the whole series up to the 30-mer within 8.2 min. The resolution of homologous oligodeoxynucleotides obtained with the monolithic column clearly surpasses that of a capillary column packed with PS-DVB-$C_{18}$ beads (Table 2, compare also FIG. 1 in Huber et al. *Anal. Chem.* 71:3730–3739 (1999)).

TABLE 2

Comparison of the Resolution Values for Oligodexynucleotides and Double-stranded DNA using Packed and Monolithic Capillary Columns

| compounds | resolution with packed column | resolution with monolithic column |
|---|---|---|
| $p(dT)_{12}/p(dT)_{13}$ | 3.05 | 5.38 |
| $p(dT)_{29}/p(dT)_{30}$ | 1.04 | 2.38 |
| 51/57 bp | 3.88 | 5.15 |
| 540/587 bp | 1.11 | 2.70 |

In this example the high-resolution capillary IP-RP-HPLC separation of phosphorylated oligodeoxynucleotide ladders was performed using a monolithic capillary column: Column, continuous PS-DVB, 60×0.20 mm ID; mobile phase, buffer A included 100 mM TEM, pH 6.97, buffer B included 100 mM TEAA, pH 6.97, 20% acetonitrile; linear gradient, 15–45% B in 3.5 min, 45–55% B in 2.5 min, 55–65% B in 4.0 min;flow-rate, 2.5 µL/min; temperature, 50° C.; detection, UV, 254 nm; sample, $p(dA)_{12\text{-}18}$, $p(dT)_{12\text{-}30}$, 40–98 fmol of each oligodeoxynucleotide.

EXAMPLE 7

Performance of Monolithic Capillary Columns for Polynucleotide Separations

Following polymerization, extensive washing with acetonitrile, and equilibration with 100 mM TEAA-5.0% acetonitrile solution, the performance of three different 60×0.20 mm ID monolithic capillary columns was compared to that of three columns packed with octadecylated, 2.3 µm micropellicular PS-DVB particles of the same dimensions. The permeabilities of the monolithic columns and the packed columns were similar resulting in back pressures between 180 and 200 bar at a flow rate of 2.6 µL/min and 50° C. column temperature, which indicates that the size of the channels for convective flow in both chromatographic beds is of approximately the same size. The relative standard deviations of the peak widths at half height both among various batches of packed capillary columns and monolithic capillary columns were better than 10% which demonstrates that column preparation was reproducible and allowed the comparison of the chromatographic performance of both column types. The chromatographic performance was evaluated by gradient separation of a mixture of $(dT)_{12\text{-}18}$ with a gradient of 5.0–12.0% acetonitrile in 100 mM TEAA in 10 min. Three injections of the standard onto each of the three columns gave average peak widths at half height for $(dT)_{18}$ of 2.28±0.22 s (sample size N=9, standard deviation sd=0.29 s, level of significance P=95%) for the monolithic columns and 3.84±0.16 s (N=9, sd=0.20 s, P=95%) for the packed bed capillary column. These values demonstrate that the chromatographic performance of monolithic columns for oligodeoxynucleotide separations is approximately 40% better than that of packed bed columns. The chromatographic efficiency of the monolithic column was determined by isocratic elution of $(dT)_{18}$ with an eluent containing 7.8% acetonitrile in 100 mM TEM at a flow rate of 2.4 µL/min. At 50° C. column temperature, the number of theoretical plates exceeded 11,500 plates for a 60 mm column, corresponding to 191,000 theoretical plates per meter.

EXAMPLE 8

Figure 4:
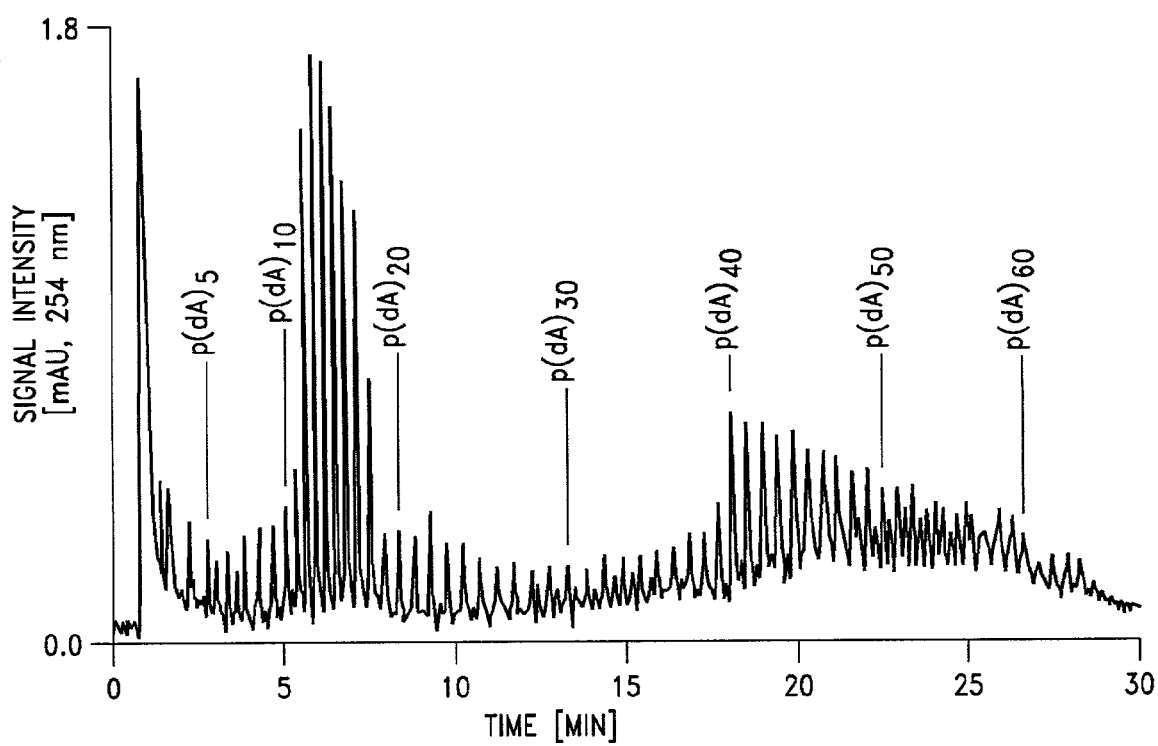
FIG. 4 is a chromatogram showing capillary IP-RP-HPLC separation of phosphorylated and dephosphorylated deoxyadenylic acids in a monolithic capillary column constructed in accordance with an embodiment of the present invention.

High-resolution Capillary IP-RP-HPLC Separation of a Mixture of Phosphorylated and Dephosphorylated Deoxyadenylic Acids The separation shown in FIG. 4 was performed under the following condition: Column, monolithic PS-DVB, 60 mm×0.20 mm ID; mobile phase, buffer A included 100 mM TEAA, pH 7.00, buffer B included 100 mM TEM, pH 7.00, 20% acetonitrile; linear gradient, 5–30% B in 5.0 min, 35–40% B in 5.0 min, 40–45% B in 6.0 min, 45–52% B in 14 min; flow-rate, 2.1 µL/min;temperature, 50° C.; detection, UV, 254 nm; sample, hydrolyzed $p(dA)_{40}$–$p(dA)_{60}$, spiked with 2.5 ng $p(dA)_{12}$–$p(dA)_{18}$.

EXAMPLE 9

Separation of Double-stranded DNA Using a PS-DVB Monolithic Column

Figure 6:
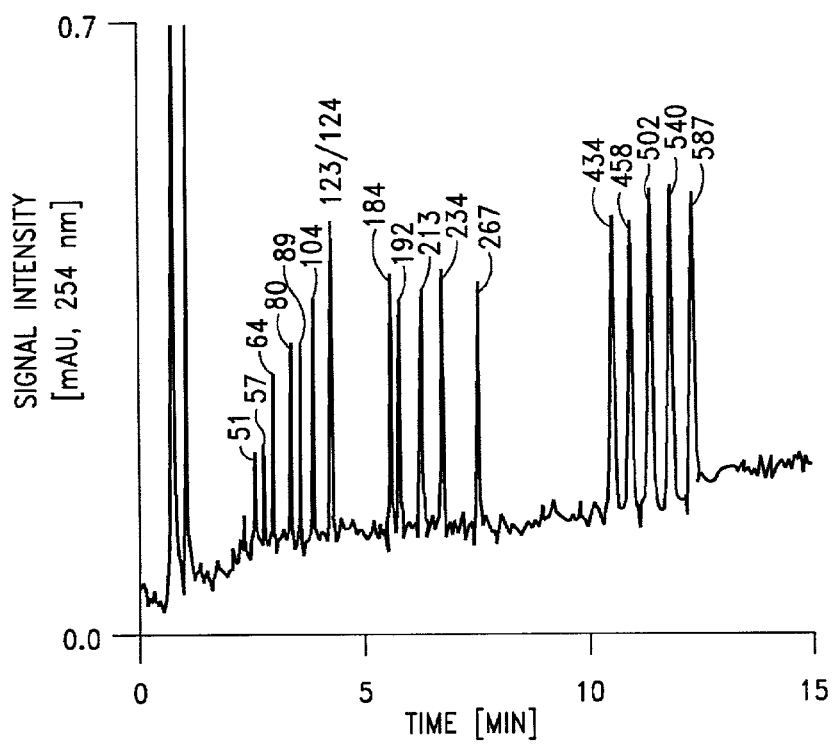
FIG. 6 is a chromatogram showing capillary IP-RP-HPLC separation of a mixture of double-stranded DNA fragments in a monolithic capillary column constructed in accordance with an embodiment of the present invention. The sample was a pBR322-Hae III digest, 1.81 fmol of each fragment.

IP-RP-HPLC has been shown to be efficient not only for the rapid separation of single-stranded oligodeoxynucleotides, but also for the fractionation of double-stranded DNA fragments up to chain lengths of 2000 bp (Huber et al. *Anal. Chem.* 67:578–585 (1995)). The applicability of the monolithic PS-DVB stationary phase to the IP-RP-HPLC separation of double-stranded DNA was tested by injection of a pBR322 DNA-Hae III digest, which was separated in 12.5 min using a gradient of 7.0–15.0% acetonitrile in 3 min, followed by 15.0–19.0% acetonitrile in 12 min in 100 mM TEM at a flow rate of 2.2 µL/min (FIG. 6). Again, the chromatogram of the mixture depicted in FIG. 6 with fragments ranging from 51–587 bp as well as the resolution values given in Table 2 demonstrate that the separation performance of monolithic columns is superior to that of packed-bed columns with respect to their separation capability for nucleic acids (compare also FIG. 1 in Huber et al. *Anal. Chem.* 67:578–585 (1995)).

Figure 5:
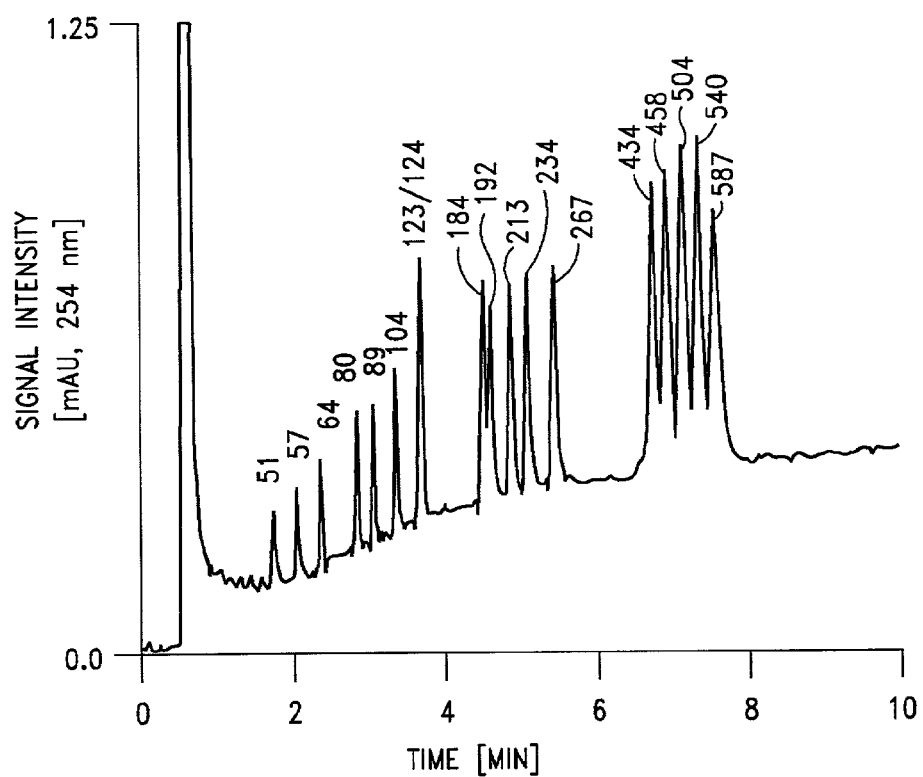
FIG. 5 is a chromatogram showing capillary IP-RP-HPLC separation of a mixture of double-stranded DNA fragments in a monolithic capillary column constructed in accordance with an embodiment of the present invention. The sample was a pBR322-Hae III digest, 4.5 fmol of each fragment.

The separation shown in FIG. 5 was performed under the following conditions: Column, continuous PS-DVB, 60×0.20 mm ID; mobile phase, buffer A 100 mM TEAA, pH 7.00, buffer B 100 mM TEM, pH 7.00, 20% acetonitrile; linear gradient, 37–67% B in 3.0 min, 67–87% B in 7.0 min;flow-rate, 3.1 µL/min;temperature, 50° C.; detection, UV, 254 nm; sample, pBR322 DNA-Hae III digest, 12.1 ng, 4.5 fmol of each fragment.

The separation shown in FIG. 6 was performed under the following conditions: Column, continuous PS-DVB, 60×0.20 mm ID; mobile phase, buffer A 100 mM TEM, pH 7.00, buffer B 100 mM TEM, pH 7.00, 20% acetonitrile; linear gradient, 35–75% B in 3.0 min, 75–95% B in 12.0 min;flow-rate,2.2 µL/min;temperature, 50° C.; detection, UV, 254 nm; sample, pBR322 DNA-Hae III digest, 1.81 fmol of each fragment.

EXAMPLE 10

Electrospray Ionization Mass Spectrometry and Coupling with Capillary Liquid Chromatography ESI-MS was performed on a Finnigan MAT LCQ quadrupole ion trap mass spectrometer (Finnigan MAT, San Jose, Calif., USA, used in FIGS. 10–17) or a Finnigan MAT TSQ 7000 triple quadrupole mass spectrometer (used in FIGS. 5 and 6) equipped with an electrospray ion source. The capillary column was directly connected to the spray capillary (fused silica, 105 μm OD, 40 μm ID, Polymicro Technologies) by means of a microtight union (Upchurch Scientific, Oak Harbor, Wash., USA). A syringe pump equipped with a 250 μL glass syringe (Unimetrics, Shorewood, Ill., USA) was used for continuous infusion experiments and for pumping sheath liquid. For analysis with pneumatically assisted ESI, an electrospray voltage of 3.2–3.7 kV and a nitrogen sheath gas flow of 20–30 arbitrary units (LCQ) or 28–33 psi (TSQ) were employed. The temperature of the heated capillary was set to 200° C. Total ion chromatograms and mass spectra were recorded on a personal computer with the LCQ Navigator software version 1.2 or on a DEC-Alpha 3000 workstation with the ICIS software version 8.3.0 (Finnigan). Mass calibration and coarse tuning was performed in the positive ion mode by direct infusion of a solution of caffeine (Sigma, St. Louis, Mo., USA), methionyl-arginyl-phenylalanyl-alanine (Finnigan), and Ultramark 1621 (Finnigan). Fine tuning for ESI-MS of oligodeoxynucleotides in the negative ion mode was performed by infusion of 3.0 μL/min of a 20 pmol/μL solution of $(dT)_{24}$ in 25 mM aqueous TEAB containing 10% acetonitrile (v/v). A sheath flow of 3.0 μL/min acetonitrile was added through the triaxial electrospray probe. For all direct infusion experiments, cations present in the oligodeoxynucleotide samples were removed by on-line cation-exchange using a 20×0.50 mm ID cation-exchange microcolumn packed with 38–75 μm Dowex 50 WX8 particles (Serva, Heidelberg, Germany) (Huber et al. M. R. *Anal. Chem.* 70:5288–5295 (1998)). For IP-RP-HPLC-ESI-MS analysis, oligodeoxynucleotides and DNA fragments were injected without prior cation removal.

EXAMPLE 11

On-line Separation and Mass Determination of Synthetic Oligodeoxynucleotides

Figure 10:
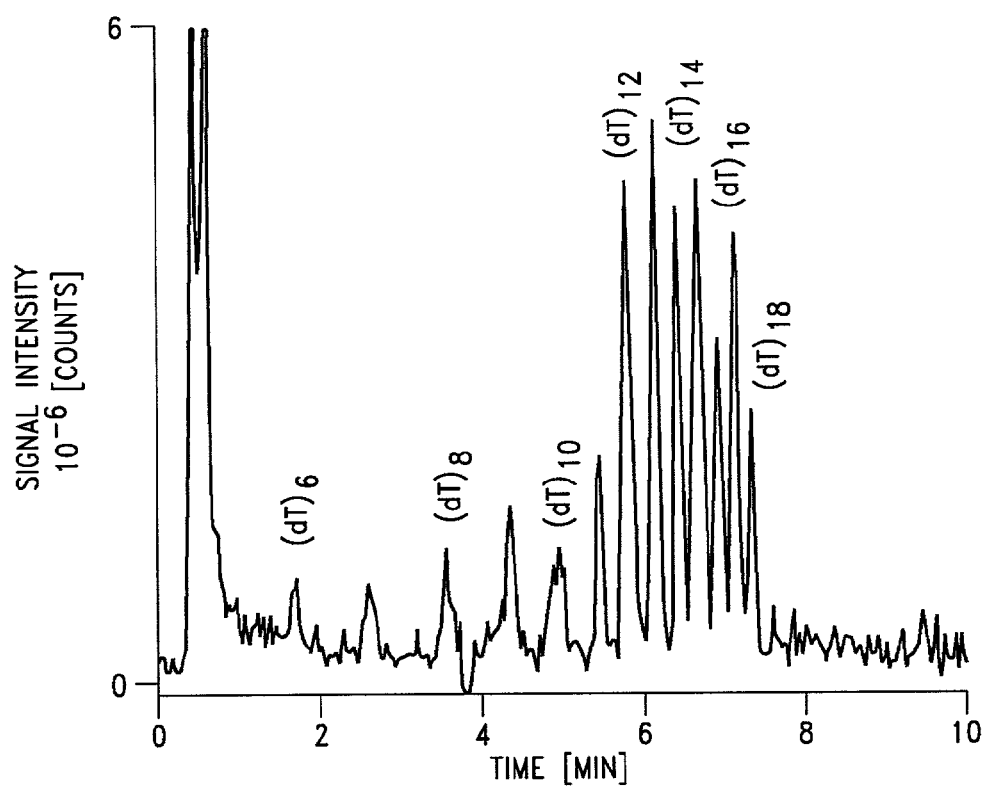
FIG. 10 illustrates the separation and mass analysis of a series of oligothymidylic acids.

For many of the analytical problems encountered with oligodeoxynucleotides, chromatographic separation in combination with UV detection is not sufficient to get a conclusive answer. The on-line conjugation of chromatographic separation to mass spectrometry, however, offers a potent tool for the characterization and identification of oligodeoxynucleotides on the basis of accurate mass determinations and fragmentation patterns. For example, the HPLC-UV analysis of a $(dT)_{12-18}$ standard that was left overnight at room temperature showed a number of small peaks eluting before the seven major peaks (chromatogram not shown). Applicants supposed that the small peaks were phosphorylated or non-phosphorylated hydrolysis products of $(dT)_{12-18}$, but this assumption was not definitive until the separation system was on-line coupled to ESI-MS, which revealed that they were non-phosphorylated hydrolyzates ranging from the 6-mer to the 11-mer (FIG. 10). Application of a gradient from 4.0–12.0% acetonitrile in 10 mM TEM enabled the separation of all oligothymidylic acids from the 6-mer to the 18-mer. Acetonitrile was added post-column as sheath liquid to enhance the mass spectrometric detectability of the separated oligodeoxynucleotides (Huber et al. *J. Chromatogr. A* 870:413–424 (2000)). This example demonstrates that by using on-line IP-RP-HPLC-ESI-MS, the unequivocal identification of low femtomol amounts of oligodeoxynucleotides is feasible on the basis of their molecular masses (Table 3).

TABLE 3

Measured and Theoretical Masses of $(dT)_{6-18}$

| oligodeoxy-nucleotide | retention time (min) | molecular mass | | relative deviation (%) |
|---|---|---|---|---|
| | | measured | theoretical | |
| $(dT)_6$ | 1.77 | 1763.09 | 1763.21 | 0.006 |
| $(dT)_7$ | 2.63 | 2066.96 | 2067.40 | 0.021 |
| $(dT)_8$ | 3.59 | 2371.90 | 2371.59 | −0.013 |
| $(dT)_9$ | 4.35 | 2675.28 | 2675.79 | 0.019 |
| $(dT)_{10}$ | 4.94 | 2978.95 | 2979.98 | 0.035 |
| $(dT)_{11}$ | 5.44 | 3284.43 | 3284.18 | −0.008 |
| $(dT)_{12}$ | 5.76 | 3589.29 | 3588.37 | −0.026 |
| $(dT)_{13}$ | 6.13 | 3892.78 | 3892.57 | −0.006 |
| $(dT)_{14}$ | 6.39 | 4197.47 | 4196.76 | −0.017 |
| $(dT)_{15}$ | 6.66 | 4501.81 | 4500.96 | −0.019 |
| $(dT)_{16}$ | 6.92 | 4806.26 | 4805.15 | −0.023 |
| $(dT)_{17}$ | 7.12 | 5109.19 | 5109.35 | 0.003 |
| $(dT)_{18}$ | 7.35 | 5413.35 | 5413.54 | 0.004 |

The separation shown in FIG. 10 was performed under the following conditions: Column, continuous PS-DVB, 60×0.20 mm ID; mobile phase, buffer A 10 mM TEM, pH 7.00, buffer B 10 mM TEM, pH 7.00, 20% acetonitrile; linear gradient, 20–60% B in 10.0 min;flow-rate, 3.2 μL/min; temperature, 50° C.; scan, 800–2000 amu in 2 s; electrospray voltage, 3.8 kV; sheath gas, 34 psi $N_2$; sheath liquid, acetonitrile; flow rate, 3.0 μL/min; sample, $(dT)_{6-18}$, 50 ng.

EXAMPLE 12

On-line Coupling of Chromatographic Separation to Mass Spectrometry

Figure 11:
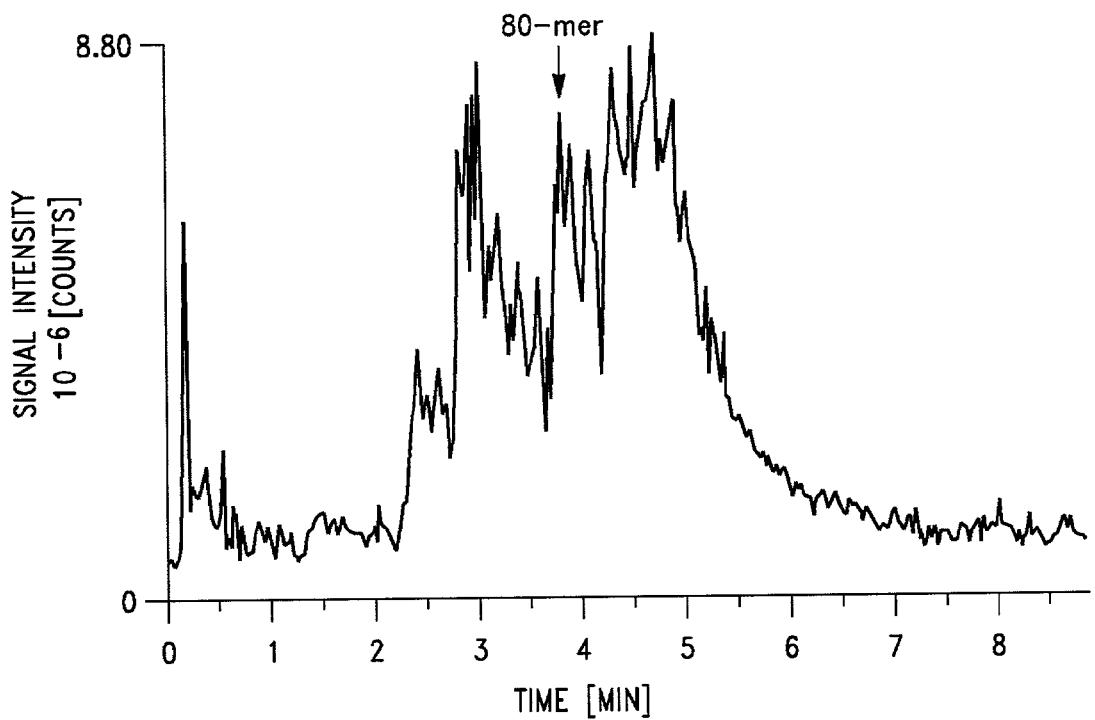
FIG. 11 is a chromatogram showing analysis of a crude synthetic 80-mer oligodeoxynucleotide by on-line IP-RP-HPLC-ESI-MS.
Figure 12:
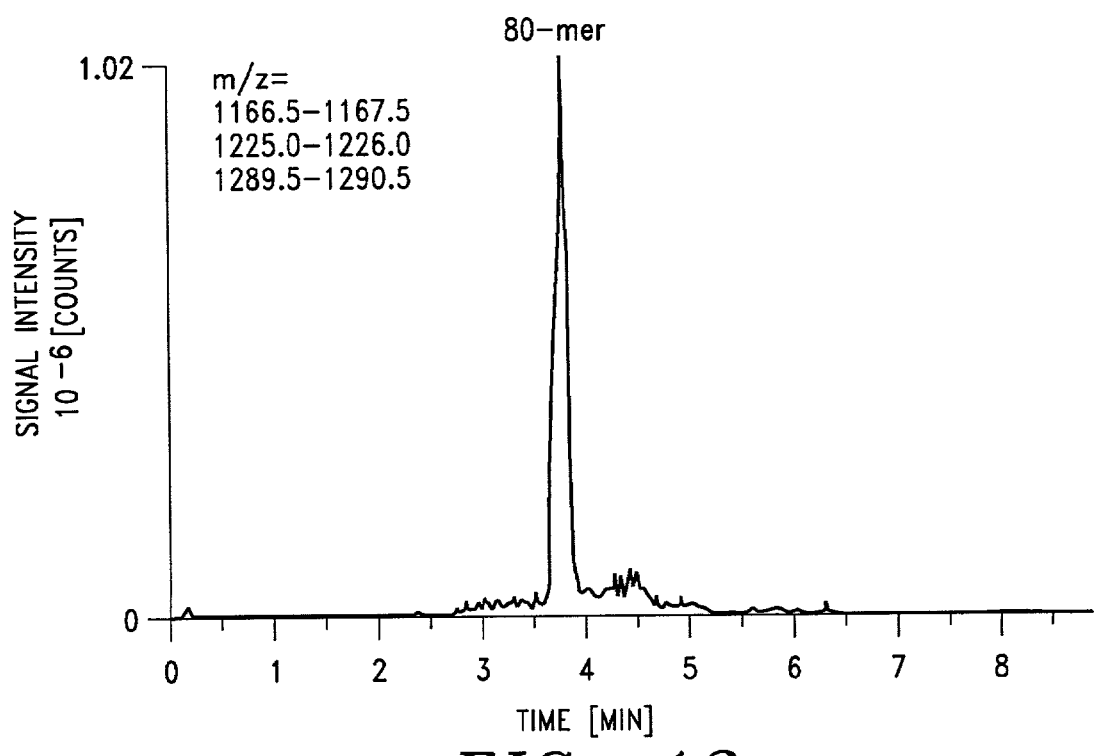
FIG. 12 is a chromatogram showing extraction of selected ion chromatograms from the data shown in FIG. 11.

Refined chemistry has significantly improved the efficiency of automated solid-phase synthesis of long oligodeoxynucleotide sequences. However, assuming a coupling efficiency of 98–99% per synthesis cycle, the maximum yield of an 80-mer oligodeoxynucleotide will be only 20–45%, and contamination of the target sequence with a number of failure sequences or partially deprotected sequences is generally observed (Huber et al. *Anal. Chem.* 71:3730–3739 (1999); Huber et al. *LC GC Int.* 14:114–127 (1996)).[28,40] FIG. 11 illustrates the analysis of 5.0 pmol of a crude 80-mer oligodeoxynucleotide. The high number of partly resolved peaks eluting between 2 and 6 min made identification and quantitation of the target sequence from the reconstructed ion chromatogram impossible. However, extraction of a selected ion chromatogram at m/z 1167.0, 1225.5, and 1290.0 clearly identified the target sequence eluting at 3.8 min (FIG. 12). Averaging and deconvolution of four mass spectra between 3.7 and 3.8 min yielded a molecular mass of 24,525.0 (FIG. 13 which correlates well with a theoretical mass of 24,527.17 (0.009% relative deviation). Moreover, the deconvoluted mass spectrum (FIG. 13) did not show notable cation adduction which verifies that IP-RP-HPLC is an efficient method for the desalting of oligodeoxynucleotides. Comparison of the mass spectrum extracted from the chromatogram (FIG. 13) to that of an 80-mer obtained by direct infusion ESI-MS (compare FIG. 3 in Huber et al. *Anal. Chem.* 70:5288–5295 (1998)) clearly corroborates the high value of on-line coupling of chromatographic separation to mass spectrometry, because the chemical background in the mass spectrum is greatly reduced upon chromatographic separation and exact mass measurement is possible using IP-RP-HPLC-ESI-MS with only one fiftieth of the amount of sample that is consumed during direct infusion ESI-MS.

Figure 13:
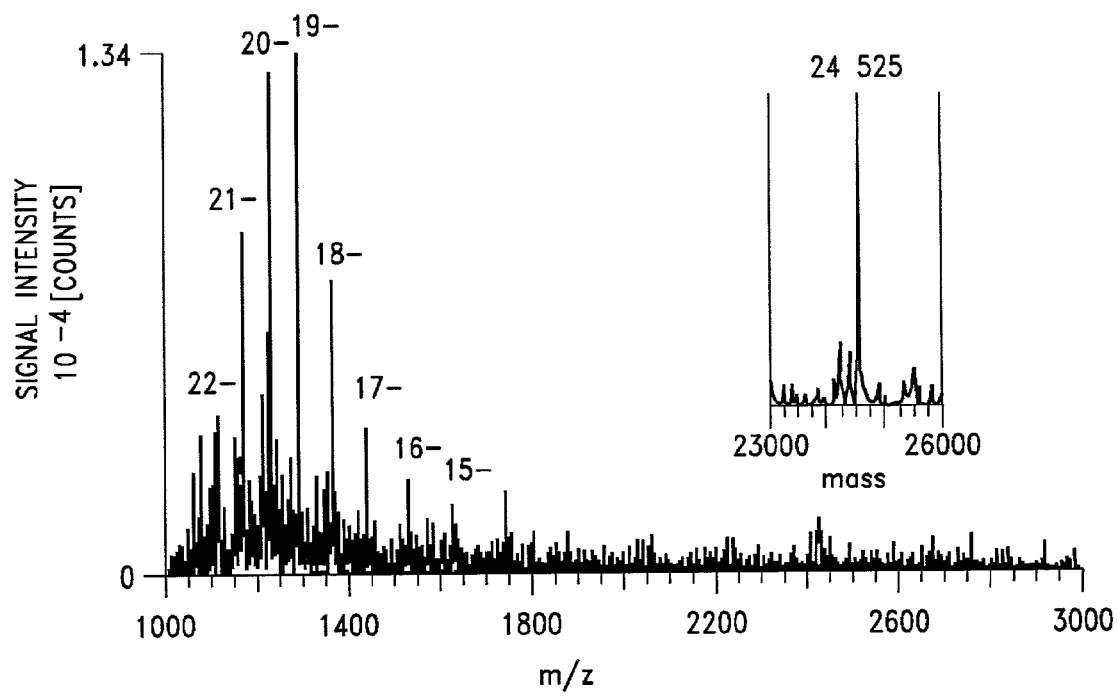
FIG. 13 is a chromatogram showing averaging and deconvolution of four mass spectra between 3.7 and 3.8 min from FIG. 11.

The separations shown in FIGS. 11–13 were performed under the following conditions: Column, continuous PS-DVB, 60×0.20 mm ID; mobile phase, buffer A 25 mM TEAB, pH 8.40, buffer B 25 mM TEAB, pH 8.40, 20% acetonitrile; linear gradient, 20–100% B in 15 min;flow-rate, 3.0 μL/min;temperature, 50° C.; scan, 1000–3000 amu; electrospray voltage, 3.2 kV; sheath gas, 30 units; sheath liquid, acetonitrile; flow rate, 3.0 μL/min; sample, 5.0 pmol raw product.

EXAMPLE 13

On-line Separation and Mass Determination of dsDNA Fragments

Figure 14:
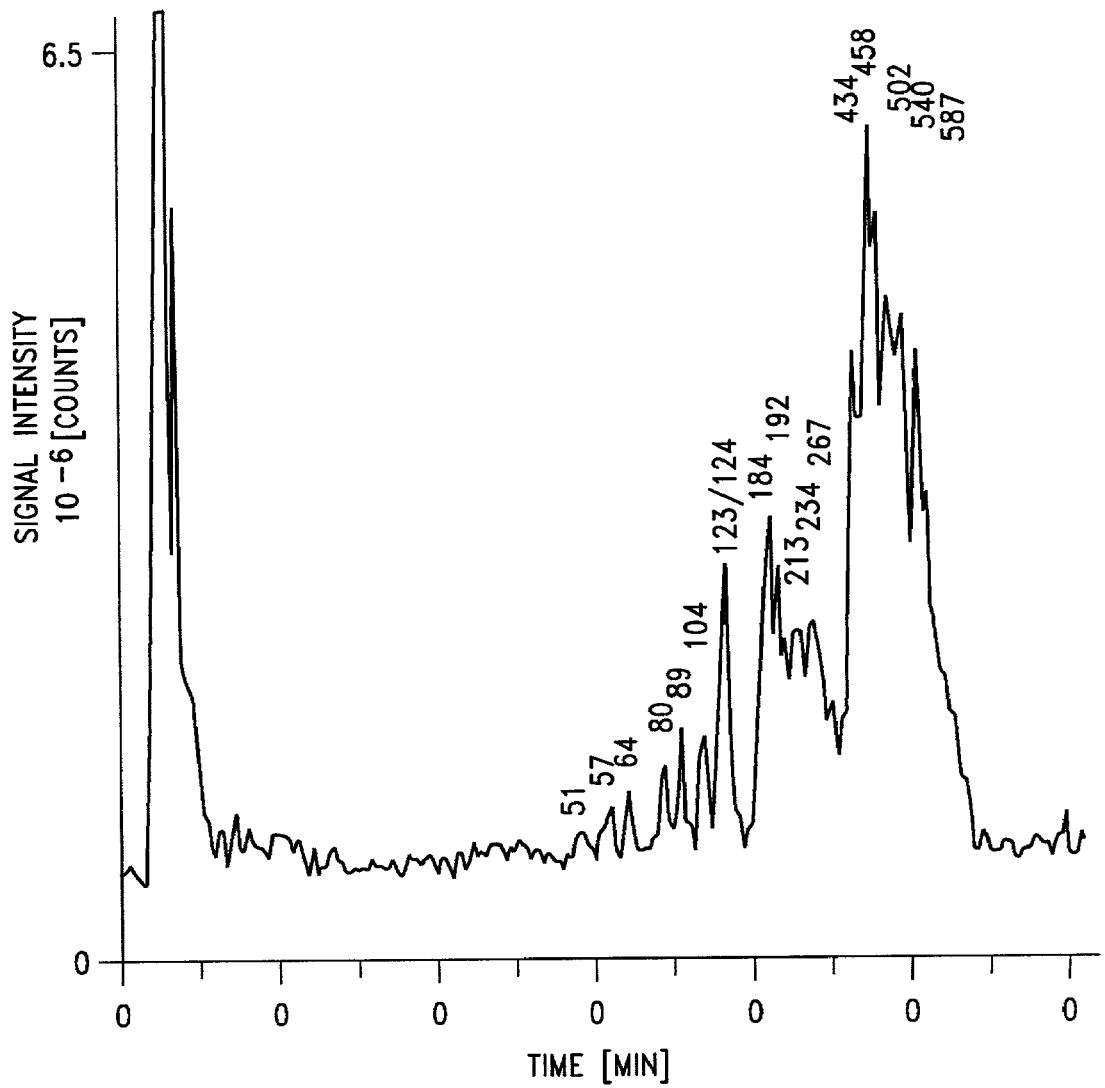
FIG. 14 is a chromatogram showing the separation and mass analysis of double-stranded DNA fragments from a Hae III digest of pBR322 plasmid (180 fmol of each fragment).

FIG. 14 illustrates the chromatogram of DNA fragments from 486 ng (180 fmol) of a pBR322 DNA-Hae III restriction digest with detection by ESI-MS. For this separation, the gradient was ramped from 3.0–6.0% acetonitrile in 3.0 min, followed by 6.0–10.0% acetonitrile in 12 min at a flow rate of 2.8 μL/min and a column temperature of 40° C. The elution conditions for the spectra shown in FIGS. 14–17 were as follows: Column, continuous PS-DVB, 60×0.20 mm ID; mobile phase, buffer A 25 mM TEAB, pH 8.40, buffer B 25 mM TEAB, pH 8.40, 20% acetonitrile; linear gradient, 15–30% B in 3.0 min, followed by 30–50% B in 12 min;flow-rate, 2.8 μL/min; temperature, 40° C.; scan, 1000–3000 amu; electrospray voltage, 3.2 kV; sheath gas, 32 units; sheath liquid, acetonitrile; flow rate, 3 μL/min; sample, pBR322 DNA-Hae III digest, 180 fmol of each fragment.

Figure 15:
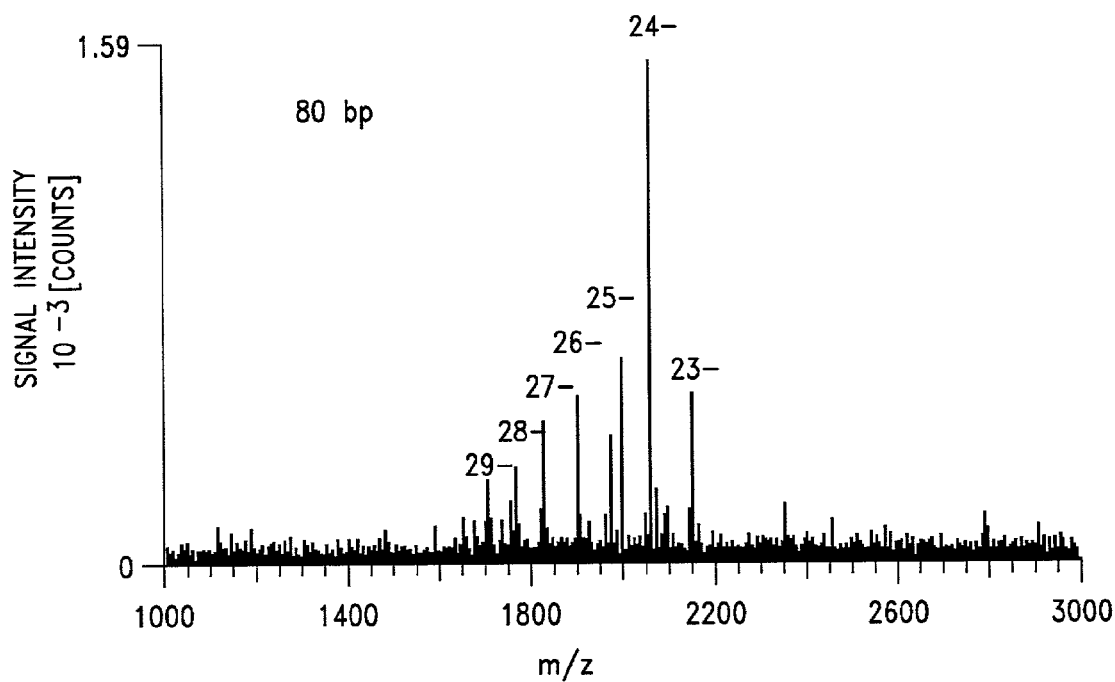
FIG. 15 shows extracted and deconvoluted mass spectra of the 80 pb fragment of the pBR322 DNA-Hae III digest under the same analysis conditions as in FIG. 14.
Figure 16:
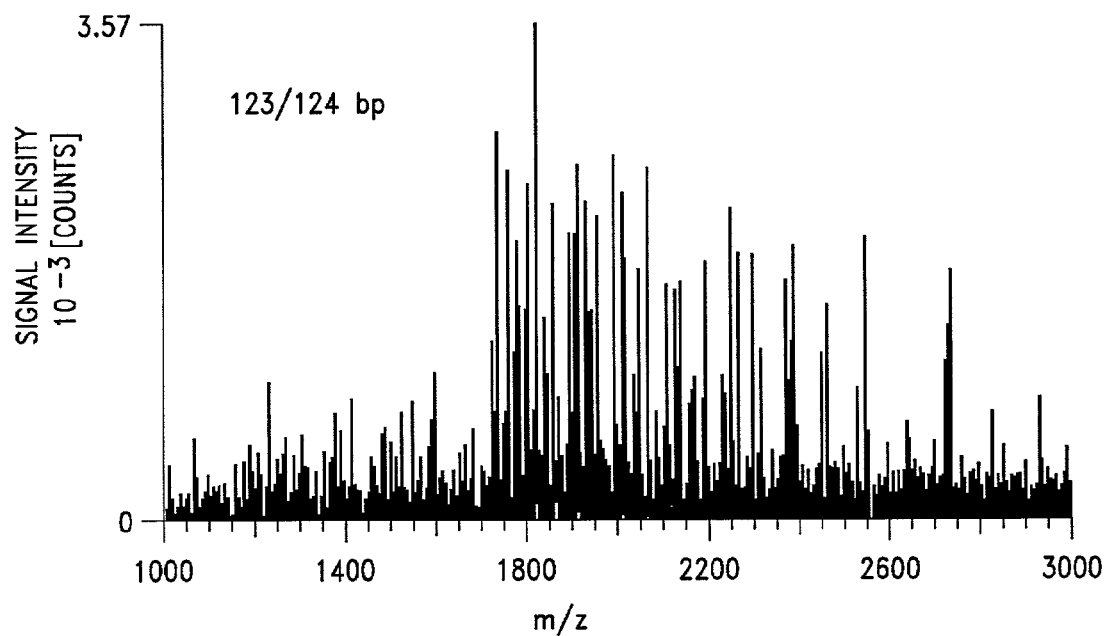
FIG. 16 shows extracted and deconvoluted mass spectra of the 123/124 pb fragment of the pBR322 DNA-Hae III digest under the same analysis conditions as in FIG. 14.
Figure 17:
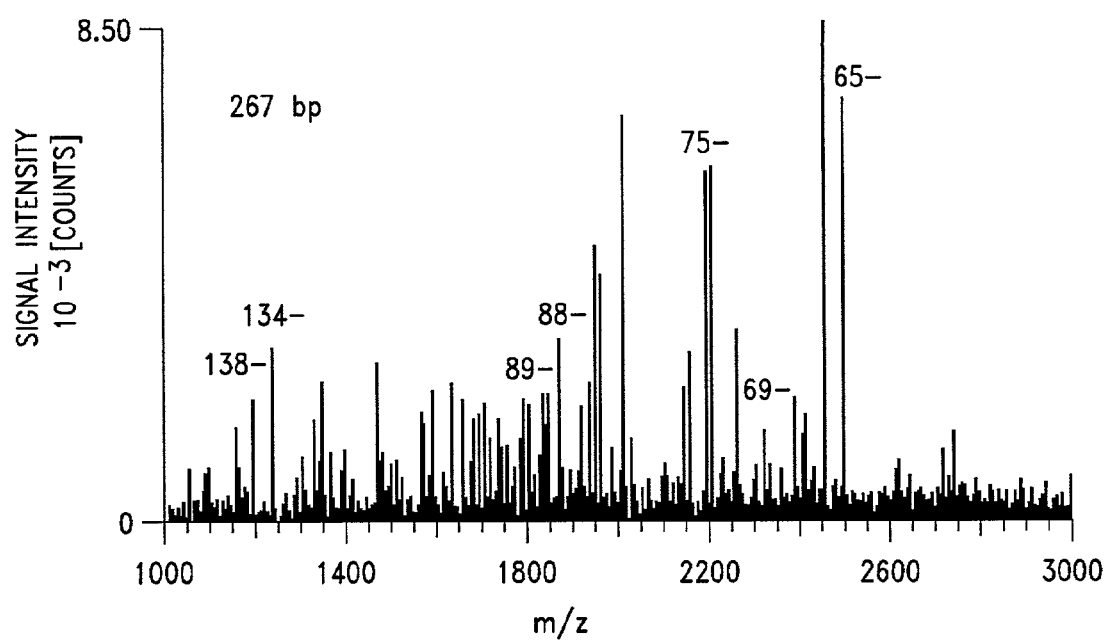
FIG. 17 shows extracted and deconvoluted mass spectra of the 267 pb fragment of the pBR322 DNA-Hae III digest under the same analysis conditions as in FIG. 14.

It can be seen that the fragments from 51–123 bp were completely resolved in the chromatogram, whereas the separation of the longer fragments was incomplete due to overloading of the column (Oberacher, H.; Krajete, A.; Parson, W.; Huber, C. G. J. Chromatogr. A submitted (2000)). Mass spectra were extracted from the reconstructed ion chromatogram by averaging 4–8 scans and three examples for fragments ranging in size from 80 to 267 bp are illustrated in FIGS. 15–17. Whereas relatively few charge states (23--29-) were found in the mass spectrum of an 80 bp fragment (FIG. 15), the number of observed signals rapidly increased with the size of the DNA fragments (FIGS. 16 and 17). The appearance of all charge state signals with sharp and defined peak shapes indicates, that cation adducts have been efficiently removed by IP-RP-HPLC.

The molecular mass of the DNA fragments was calculated by a three step procedure. First, a rough molecular mass was obtained by automatic deconvolution of the raw spectrum using the Bioworks software application. For the fragments from 51–267 bp this deconvolution step readily yielded definite mass information and even the mass spectrum of the coeluting 123 bp and 124 bp fragments was easily deconvoluted into two separate mass peaks. For the longer DNA fragments (434–587 bp), signals for the individual charge states could be only identified using the knowledge of the theoretical molecular mass of the investigated fragments from their DNA sequence. Subsequently, the charge states of all m/z signals in the mass spectrum having an abundance more than five times the signal-to-noise ratio were calculated. Finally, the m/z values and the corresponding integer charges state were used to calculate a molecular mass. Statistical treatment of the molecular masses of the individual charge states gave the average molecular mass and its standard deviation. The results of these calculations are summarized in (Table 4), which shows that the masses of the double-stranded DNA fragments ranging in size up to 267 bp were measured with an accuracy of better than 0.08%.

TABLE 4

Molecular Masses of Double-stranded DNA Fragments from the pBR322 DNA-Hae III Digest

| | | molecular mass | | relative deviation |
|---|---|---|---|---|
| fragment | position[a] | measured[b] | theoretical | (%) |
| 51 | 942–992 | 31,565 ± 24 (4) | 31,559.57 | 0.018 |
| 57 | 993–1049 | 35,252 ± 54 (6) | 35,263.04 | −0.032 |
| 64 | 534–597 | 39,573 ± 84 (7) | 39,592.83 | −0.026 |
| 80 | 3410–3489 | 49,494 ± 43 (10) | 49,475.35 | 0.038 |
| 89 | 832–920 | 55,058 ± 41 (14) | 55,038.97 | 0.034 |
| 104 | 298–401 | 64,391 ± 56 (22) | 64,312.99 | 0.12 |
| 123 | 175–297 | 76,059 ± 49 (15) | 76,045.76 | 0.017 |
| 124 | 402–525 | 76,731 ± 44 (17) | 76,675.05 | 0.073 |
| 184 | 1263–1446 | 113,802 ± 140 (15) | 113,747.36 | 0.048 |
| 192 | 4344–174 | 118,722 ± 123 (17) | 118,668.82 | 0.045 |
| 213 | 1050–1262 | 131,733 ± 148 (18) | 131,674.02 | 0.045 |
| 234 | 598–831 | 144,708 ± 127 (25) | 144,646.56 | 0.042 |
| 267 | 3490–3756 | 165,091 ± 230 (12) | 165,019.11 | 0.044 |
| 434 | 2518–2951 | n.d.[c] | 268,240.41 | n.d. |
| 458 | 2952–3409 | n.d. | 283,002.81 | n.d. |
| 502 | 1447–1948 | n.d. | 310,240.12 | n.d. |
| 540 | 1949–2488 | n.d. | 333,738.33 | n.d. |
| 587 | 3757–4343 | n.d. | 362,707.09 | n.d. |

[a]position relative to the EcoR I restriction site in pBR322.
[b]molecular mass given as average ± standard deviation (number of charge states used to calculate the average molecular mass).
[c]not determined.

EXAMPLE 14

IP-RP-HPLC-ESI-MS/MS Sequencing of Oligodeoxynucleotides

Figure 18:
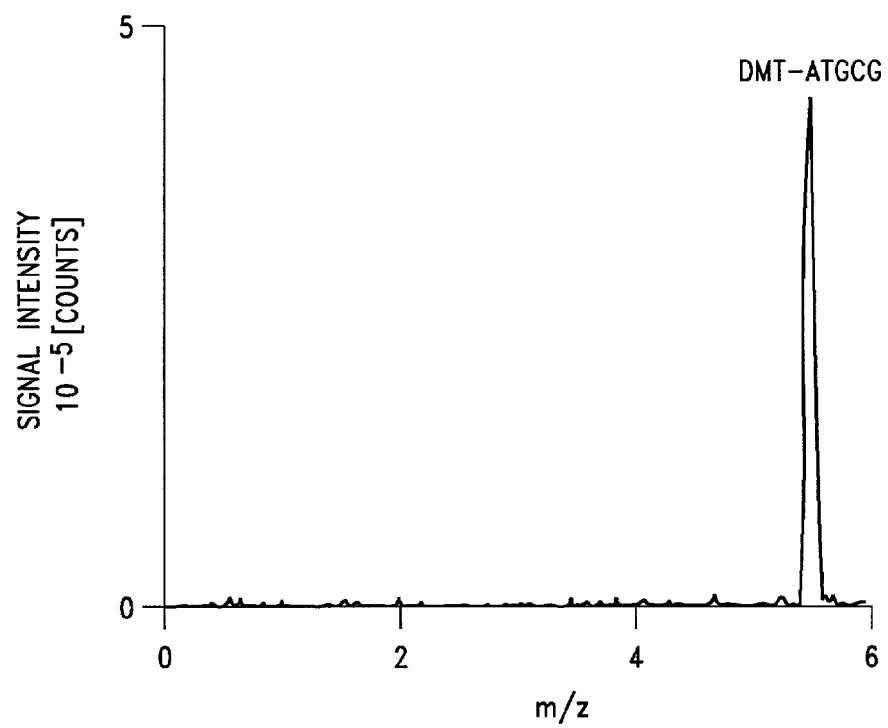
FIG. 18 illustrates IP-RP-HPLC-MS analysis of an unfragmented 5-mer oligodeoxynucleotide.
Figure 19:
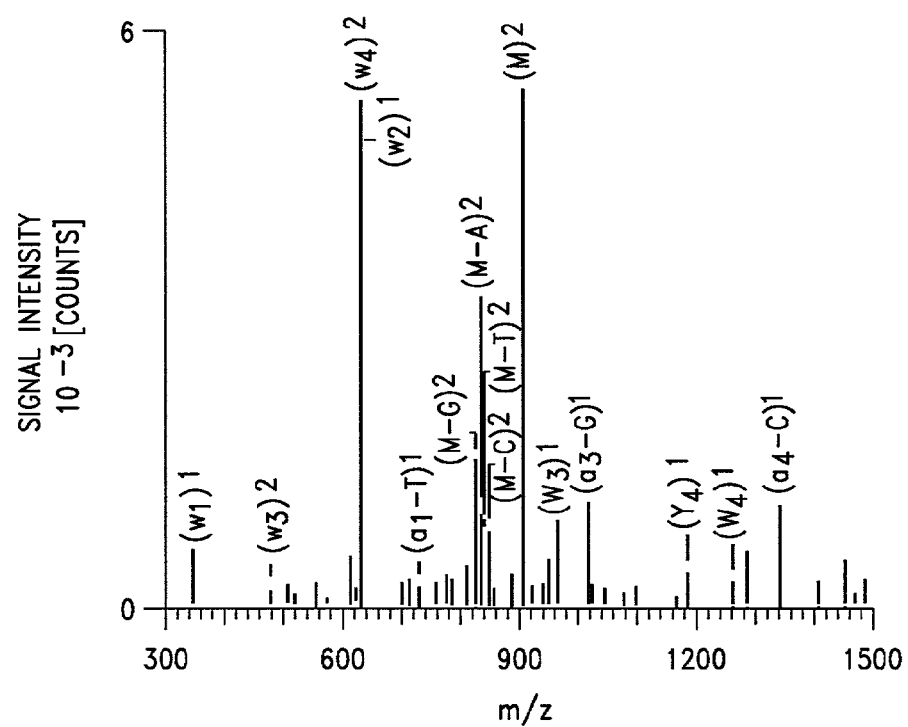
FIG. 19 shows a mass spectrum obtained from IP-RP-HPLC-ESI-MS/MS analysis.

In addition to information regarding the molecular mass, tandem mass spectrometry (MS/MS) utilizing collisionally induced dissociation (CID) provides valuable information about the base sequence of oligodeoxynucleotides (McLuckey et al. *Tandem Mass Spectrometry of Small, Multiply Charged Oligodeoxynucleotides* 3:pp 60–70 (1992); Griffey et al. *J. Mass Spectrom.* 32:305–313 (1997)). In this example, for the application of monolithic capillary columns in nucleic acid analysis, the feasibility to perform on-line MS/MS experiments on oligodeoxynucleotides upon liquid chromatographic separation was examined. To evaluate the performance of IP-RP-HPLC-ESI-MS/MS for oligodeoxynucleotide sequencing, a 5-mer oligodeoxynucleotide (sequence 5'-ATGCG-3') was ordered from Microsynth. The IP-RP-HPLC-ESI-MS analysis of the unfragmented 5-mer gave a molecular mass of 1805.00, which exceeded the expected mass value of 1503.04 by 301.96 mass units. This mass difference could be attributable to an additional thymidine residue (probably entered into the synthesis automat by accident) or to a 5'-terminal dimethoxytrityl protecting group (that has been forgotten to hydrolyze after the last coupling cycle). Substantially increased retention in the chromatographic analysis was indicative for the latter assumption. The presence of a dimethoxytrityl protecting group as well as the total sequence of the oligodeoxynucleotide was confirmed using IP-RP-HPLC-ESI-MS/MS (FIGS. 18 and 19). The ESI-MS/MS experiment was performed by isolating the $[M-2H]^{2-}$ charge state at m/z 901.37 and collisional activation at 19% relative collision energy. Assignments and masses for the fragment ions observed in the tandem mass spectrum (FIG. 19) are listed in Table 5.

TABLE 5

Fragment Ions for Sequencing of a 5-mer Oligodeoxynucleotide

| Ion assignment | m/z |
|---|---|
| $(M)^{2-}$ | 901.37 |
| $(M-A)^{2-}$ | 833.65 |
| $(M-T)^{2-}$ | 838.57 |
| $(M-G)^{2-}$ | 826.13 |
| $(M-C)^{2-}$ | 845.89 |
| $(w_1)^{1-}$ | 345.87 |

TABLE 5-continued

Fragment Ions for Sequencing of a 5-mer Oligodeoxynucleotide

| Ion assignment | m/z |
|---|---|
| $(w_2)^{1-}$ | 635.06 |
| $(w_3)^{1-}$ | 964.18 |
| $(w_4)^{1-}$ | 1267.01 |
| $(w_3)^{2-}$ | 481.45 |
| $(w_4)^{2-}$ | 633.53 |
| $(a_2-T)^{1-}$ | 714.16 |
| $(a_3-G)^{1-}$ | 1016.07 |
| $(a_4-C)^{1-}$ | 1345.98 |

Beside the parent ion all four ions that show loss of one nucleobase are observed. The most diagnostic ions however arise from fragmentation which produces w series ions, that are used to determine the 3'→5' sequence and the $a_n$-$B_n$ series ions, that are used to determine the 5'→3' sequence (McLuckey et al. *Tandem Mass Spectrometry of Small, Multiply Charged Oligodeoxynucleotides* 3:60–70 (1992)). The complete w series is present in the MS/MS spectrum and the masses correspond to those expected for an oligodeoxynucleotide with the sequence 5'-ATGCG-3', proving that the 3' terminus is unmodified. The $a_n$-$B_n$, series however shows a mass shift of +302 from the expected mass, corresponding to the presence of the dimethoxytrityl protecting group at the 5' terminus. Finally the presence of the protective group was confirmed by cleavage with 2% formic acid at room temperature for 5 minutes, yielding the oligodeoxynucleotide ATGCG with the expected mass of 1502.98.

The separations shown in FIGS. 18 and 19 were performed under the following conditions: Column, continuous PS-DVB, 60×0.20 mm ID; mobile phase, buffer A 25 mM TEAB, pH 8.40, buffer B 25 mM TEAB, pH 8.40, 20% acetonitrile; linear gradient, 10–100% B in 5.0 min;flow-rate, 3.0 µL/min; temperature, 50° C.; daughter ions of m/z 901.5, 4.0 amu isolation width, 19% relative collision energy; scan, 250–1810 amu; electrospray voltage, 3.2 kV; sheath gas, 30 units; sheath liquid, acetonitrile; flow rate, 3.0 µL/min; sample, 25 pmol raw product.

While the foregoing has presented specific embodiments of the present invention, it is to be understood that these embodiments have been presented by way of example only. It is expected that others will perceive and practice variations which, though differing from the foregoing, do not depart from the spirit and scope of the invention as described and claimed herein.

What is claimed is:

1. A device for separating a mixture of polynucleotides, said device comprising:
   a polymeric monolith having non-polar chromatographic surfaces devoid of micropores,
   wherein said monolith comprises an underivatized poly (styrene-divinylbenzene) matrix,
   wherein said monolith is contained within a fused silica tube having an inner diameter in the range of 1 micrometer to 1000 micrometer, wherein said monolith is immobilized by covalent attachment at the inner wall of said tube.

2. A device of claim 1 wherein said tube is devoid of retaining frits.

3. A device of claim 1 wherein said monolith is characterized by having 100,000 to 200,000 theoretical plates per meter.

4. A device of claim 3 wherein said theoretical plates per meter is determined from the retention time of single stranded $p(dT)_{18}$ standard using the following equation:

$$(N/L) = (5.54/L)\left(\frac{t_R}{w_{0.5}}\right)^2$$

wherein N is the number of theoretical plates, $t_R$ is the retention time of said standard determined during an isocratic elution, $w_{0.5}$ is the peak width at half height, and L is the length of the monolith in meters.

5. A device of claim 4 wherein said tube has an inner diameter of 200 micrometer and a length of 60 mm, wherein during said isocratic elution said monolith has a back pressure in the range of 180 to 200 bar, and a flow rate in the range of 2 to 3 µL/min at an elution temperature of 50° C.

6. A device of claim 1 wherein said monolith has a surface morphology, as determined by scanning electron microscopy, that resembles the surface morphology of octadecyl modified poly(styrene-divinylbenzene) particles, wherein said surface morphology of said monolith is rugulose.

7. A device of claim 1 wherein said monolith has channels sufficiently large for convective flow of said mobile phase.

8. A device for separating a mixture of polynucleotides, said device comprising:
   a polymeric monolith having nonpolar chromatographic surfaces,
   wherein said monolith comprises an underivatized poly (styrene-divinylbenzene) matrix and is devoid of micropores,
   wherein said monolith is contained within a fused silica tube, and
   wherein said monolith is immobilized by covalent attachment at the inner wall of said tube.

9. A device of claim 8 wherein said tube has an inner diameter in the range of 1 micrometer to 1000 micrometer.

10. A device of claim 8 wherein said tube is devoid of retaining frits.

11. A device of claim 8 wherein said monolith is characterized by having 10,000 to 200,000 theoretical plates per meter.

12. A device of claim 8 wherein said monolith has a surface morphology, as determined by scanning electron microscopy, that is brush-like.

13. A device of claim 8 wherein said monolith comprises an underivatized monolithic stationary phase.

14. A device of claim 8 wherein said monolith has a surface morphology, as determined by scanning electron microscopy, that resembles the surface morphology of octadecyl modified poly(styrene-divinylbenzene) particles, wherein said surface morphology of said monolith is rugulose.

15. A device of claim 8 wherein said monolith has channels sufficiently large for convective flow of said mobile phase.

16. A device for separating a mixture of polynucleotides, said device comprising:
   a polymeric monolith having non-polar chromatographic surfaces which are devoid of micropores,
   wherein said monolith comprises an underivatized poly (styrene-divinylbenzene) matrix,
   wherein said monolith is contained within a fused silica tube,
   wherein said tube has been silanized, and
   wherein said tube is devoid of retaining frits.

17. A device of claim 16 wherein said monolith is immobilized by covalent attachment at the inner wall of said tube.

18. A device of claim 16 wherein said monolith is characterized by having 100,000 to 200,000 theoretical plates per meter.

19. A device of claim 16 wherein said monolith has a surface morphology, as determined by scanning electron microscopy, that resembles the surface morphology of octadecyl modified poly (styrene-divinylbenzene) particles, wherein said surface morphology of said monolith is brush-like.

20. A device of claim 16 wherein said tube has an inner diameter in the range of 1 micrometer to 1000 micrometer.

21. A device of claim 16 wherein said monolith has a surface morphology, as determined by scanning electron microscopy, that resembles the surface morphology of octadecyl modified poly(styrene-divinylbenzene) particles, wherein said surface morphology of said monolith is rugulose.

22. A device for separating a mixture of polynucleotides, said device comprising:
   a polymeric monolith having non-polar chromatographic surfaces which are devoid of micropores,
   wherein said monolith comprises an underivatized polystyrene divinylbenzene matrix,
   wherein said monolith is contained within a tube having an inner diameter in the range of 1 micrometer to 1000 micrometer,
   wherein said monolith is characterized by having 10,000 to 200,000 theoretical plates per meter.

23. A device of claim 22 wherein said monolith is contained within a tube having an inner diameter in the range of 10 micrometer to 500 micrometer.

24. A device of claim 22 wherein said monolith is immobilized by covalent attachment at the inner wall of said tube.

25. A device of claim 24 wherein said tube is devoid of retaining frits.

26. A device for separating a mixture of polynucleotides, said device comprising:
   a polymeric monolith having non-polar chromatographic surfaces which are devoid of micropores,
   wherein said monolith comprises an underivatized poly (styrene-divinylbenzene) matrix,
   wherein said monolith is characterized by having at least 100,000 theoretical plates per meter,
   wherein said monolith is contained within a silanized fused silica tube having an inner diameter in the range of 10 micrometer to 1000 micrometer, wherein said monolith is immobilized at the inner wall of said tube.

27. A device of claim 26 wherein said monolith is characterized by having 100,000 to 200,000 theoretical plates per meter.

28. A device of claim 26 wherein said monolith is contained within a tube having an inner diameter in the range of 1 micrometer to 1000 micrometer.

29. A device of claim 26 wherein said monolith has a surface morphology, as determined by scanning electron microscopy, that resembles the surface morphology of octadecyl modified poly(styrene-divinylbenzene) particles, wherein said surface morphology of said monolith is rugulose.

30. A miniaturized chromatographic system for separating a mixture of polynucleotides said system comprising the device of claim 26.

31. A device for separating a mixture of polynucleotides, said device comprising:
   a polymeric monolith having nonpolar chromatographic surfaces,
   wherein said monolith has a surface morphology, as determined by scanning electron microscopy, that resembles the surface morphology of octadecyl modified poly(styrene-divinylbenzene) particles, wherein said surface morphology of said monolith is rugulose and brush-like,
   wherein said monolith comprises an underivatized poly(styrene-divinylbenzene) matrix,
   wherein said monolith is contained within a fused silica tube having an inner diameter in the range of 1 micrometer to 1000 micrometer,
   wherein said monolith is immobilized at the inner wall of said tube, and
   wherein said surfaces of said monolith are non-porous.

32. A device of claim 31 wherein said tube is devoid of retaining frits.

33. A device of claim 31 wherein said monolith characterized by having 100,000 to 200,000 theoretical plates per meter.

34. A device of claim 31 wherein said tube has been silanized.

35. A device of claim 31 wherein said monolith is formed from a polymerization mixture including underivatized styrene, a crosslinking agent, and a porogen, wherein said porogen comprises tetrahydrofuran.

36. A device of claim 31 wherein said polynucleotides comprise double-stranded fragments having lengths in the range of 3 to 600 base pairs.

37. A system of claim 30 wherein said monolith is operatively coupled to a mass spectrometer.

38. A chromatographic device, said device comprising:
   a polymeric monolith having non-polar chromatographic surfaces wherein said surfaces are nonporous,
   wherein said monolith comprises an underivatized poly(styrene-divinylbenzene) matrix,
   wherein said monolith is contained within a silanized fused silica tube having an inner diameter in the range of 10 micrometer to 1000 micrometer, and wherein said monolith is immobilized at the inner wall of said tube.

* * * * *